US009681809B2

(12) United States Patent
Sharma et al.

(10) Patent No.: US 9,681,809 B2
(45) Date of Patent: *Jun. 20, 2017

(54) IMPLANTABLE MEDICAL DEVICE HAVING OPTICAL FIBER FOR SENSING ELECTRICAL ACTIVITY

(71) Applicant: Medtronic, Inc., Minneapolis, MN (US)

(72) Inventors: Vinod Sharma, Blaine, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1137 days.

This patent is subject to a terminal disclaimer.

(21) Appl. No.: 13/794,352

(22) Filed: Mar. 11, 2013

(65) Prior Publication Data

US 2013/0197373 A1    Aug. 1, 2013

Related U.S. Application Data

(63) Continuation of application No. 11/676,128, filed on Feb. 16, 2007, now Pat. No. 8,396,539.

(51) Int. Cl.
*C12Q 1/68* (2006.01)
*A61B 5/00* (2006.01)
*A61B 5/0452* (2006.01)

(52) U.S. Cl.
CPC .......... *A61B 5/0071* (2013.01); *A61B 5/0084* (2013.01); *A61B 5/0452* (2013.01)

(58) Field of Classification Search
None
See application file for complete search history.

(56) References Cited

U.S. PATENT DOCUMENTS

| | | |
|---|---|---|
| 4,106,512 A | 8/1978 | Bisping |
| 4,311,153 A | 1/1982 | Smits |
| 4,502,492 A | 3/1985 | Bornzin |
| 4,506,680 A | 3/1985 | Stokes |
| 4,593,695 A | 6/1986 | Wittkampf |
| 4,690,155 A | 9/1987 | Hess |
| 4,785,815 A | 11/1988 | Cohen |
| 4,900,303 A | 2/1990 | Lemelson |
| 4,955,382 A | 9/1990 | Franz et al. |
| 5,041,108 A | 8/1991 | Fox et al. |
| 5,213,098 A | 5/1993 | Bennett et al. |
| 5,222,493 A | 6/1993 | Sholder |
| 5,324,310 A | 6/1994 | Greeninger |
| 5,331,966 A | 7/1994 | Bennett et al. |
| 5,425,363 A | 6/1995 | Wang |
| 5,575,814 A | 11/1996 | Giele et al. |
| 5,674,217 A | 10/1997 | Wahlstrom et al. |
| 5,678,550 A | 10/1997 | Bassen et al. |
| 5,792,189 A | 8/1998 | Gray et al. |
| 5,836,989 A | 11/1998 | Shelton |
| 5,948,015 A | 9/1999 | Hess et al. |
| 6,011,984 A | 1/2000 | Van Antwerp et al. |
| 6,134,473 A | 10/2000 | Hemming et al. |
| 6,144,866 A | 11/2000 | Miesel et al. |
| 6,152,882 A | 11/2000 | Prutchi |
| 6,174,291 B1* | 1/2001 | McMahon ........... A61B 5/0071 600/564 |
| 6,347,167 B1 | 2/2002 | Hagelin |
| 6,360,126 B1 | 3/2002 | Mika et al. |
| 6,430,448 B1 | 8/2002 | Chitre et al. |
| 6,434,428 B1 | 8/2002 | Sloman et al. |
| 7,190,993 B2 | 3/2007 | Sharma et al. |
| 8,396,539 B2* | 3/2013 | Sharma ............... A61B 5/0071 356/901 |
| 2001/0049543 A1 | 12/2001 | Kroll |
| 2001/0055462 A1* | 12/2001 | Seibel ............... A61B 1/00048 385/147 |
| 2002/0007111 A1* | 1/2002 | Deckert ............ G02B 23/2407 600/177 |
| 2002/0013572 A1* | 1/2002 | Berlin ...................... A61F 2/15 606/4 |
| 2002/0019020 A1 | 2/2002 | Rhodes et al. |
| 2002/0116031 A1 | 8/2002 | Vonk |
| 2002/0157120 A1 | 10/2002 | Tsien et al. |
| 2003/0194172 A1 | 10/2003 | Khalil et al. |
| 2003/0220549 A1* | 11/2003 | Liu ...................... A61B 5/0059 600/317 |
| 2004/0098075 A1 | 5/2004 | Lee |
| 2004/0143190 A1 | 7/2004 | Schnitzer |
| 2005/0090438 A1 | 4/2005 | Brodsky |
| 2005/0096720 A1* | 5/2005 | Sharma ................. A61B 5/042 607/122 |
| 2006/0195014 A1* | 8/2006 | Seibel ................. A61B 1/0008 600/102 |

(Continued)

OTHER PUBLICATIONS

Definition of co-transfection, Dorland's Medical Dictionary for Health Consumers, 2007, Elsevier, Inc. [Retrieved on Sep. 25, 2012]. Retrieved from the Internet:<URL:http://medical-dictionary.thefreedictionary.com/p/cotransfection>; 1 pg.
International Search Report for PCT Application No. PCT/US2008/054142, Jul. 23, 2008, 5 pages.

*Primary Examiner* — Ann Lam
(74) *Attorney, Agent, or Firm* — Carol F. Barry

(57) ABSTRACT

An implantable medical device for optically sensing action potential signals in excitable body tissue. The device includes an elongated tubular lead body carrying an optical fiber extending from a proximal lead end to a distal lead end to position the optical fiber at a target site. The lead body additionally carries a conduit for dispensing a voltage-sensitive fluorescent dye into tissue surrounding the target site. The optical fiber transmits excitation light to the fluorescent dye to cause the dye to fluoresce with varying intensity as the transmembrane potentials of local tissue cells vary due to passing depolarization wavefronts. The optical fiber transmits the fluorescence signal to the device to generate an action potential signal or fiducial points of an action potential signal for use in accurately measuring and characterizing electrical activity of excitable tissue.

17 Claims, 20 Drawing Sheets

(56) References Cited

U.S. PATENT DOCUMENTS

| | | | |
|---|---|---|---|
| 2008/0058629 A1* | 3/2008 | Seibel | A61B 1/0008 600/368 |
| 2008/0082078 A1* | 4/2008 | Berlin | A61F 9/00781 604/521 |
| 2008/0275325 A1* | 11/2008 | Miyakawa | A61B 5/0071 600/368 |
| 2009/0216097 A1* | 8/2009 | Wilson | A61B 5/14539 600/327 |

* cited by examiner

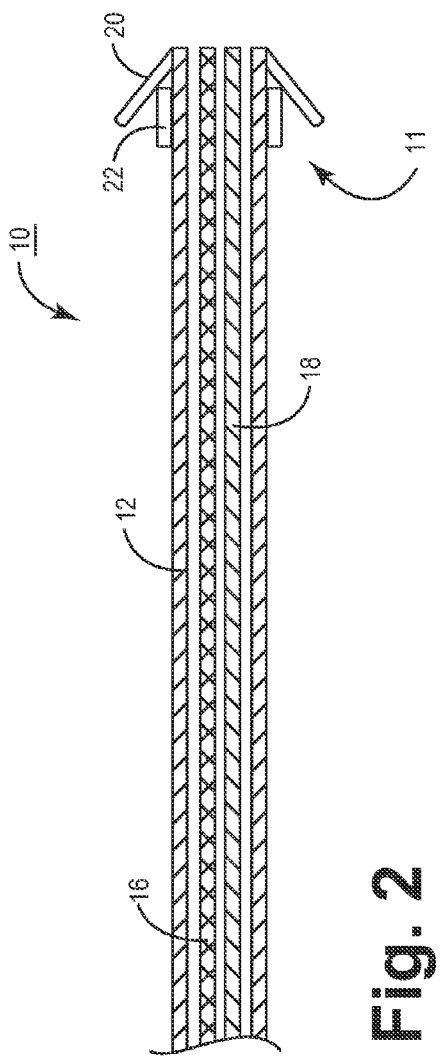
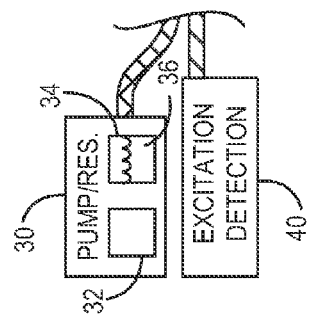
Fig. 2
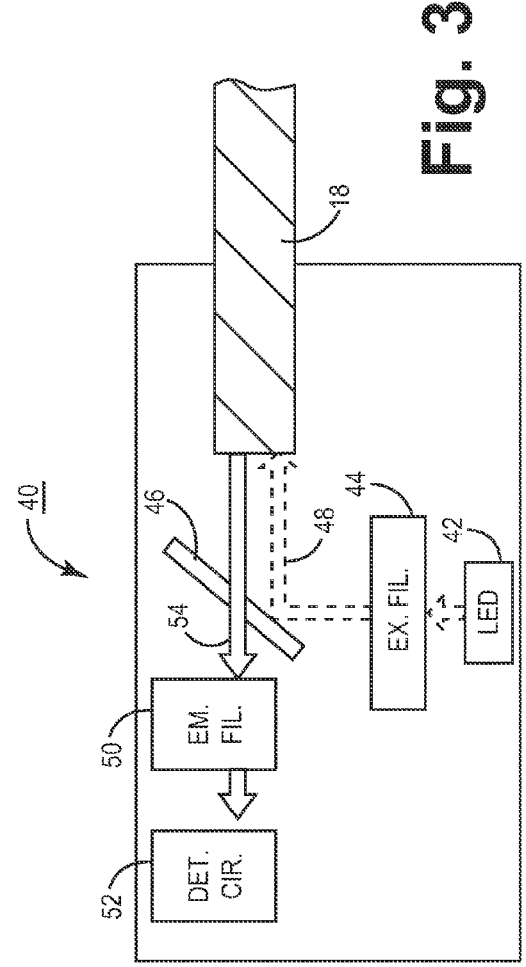
Fig. 3

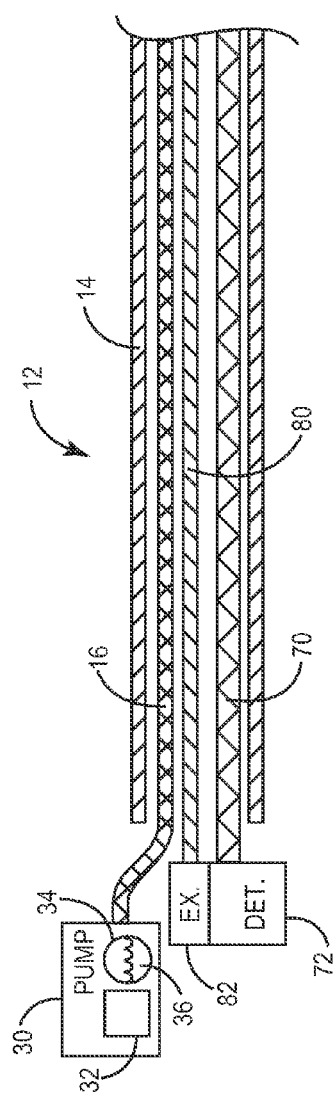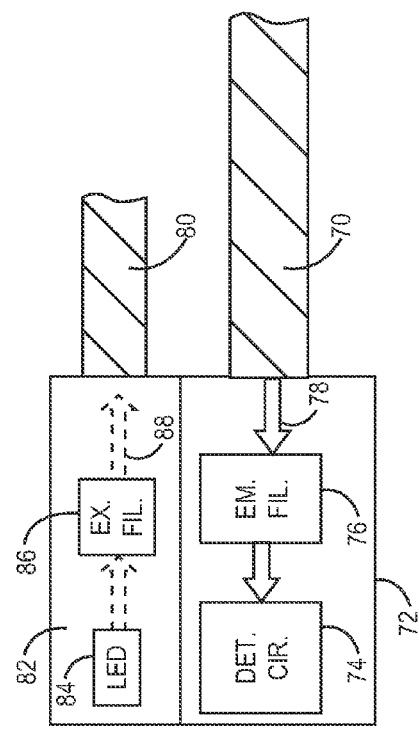
Fig. 4
Fig. 5

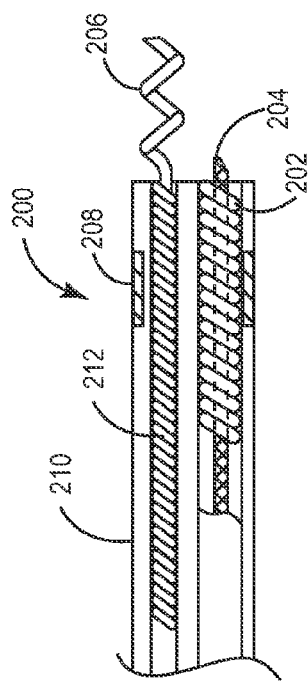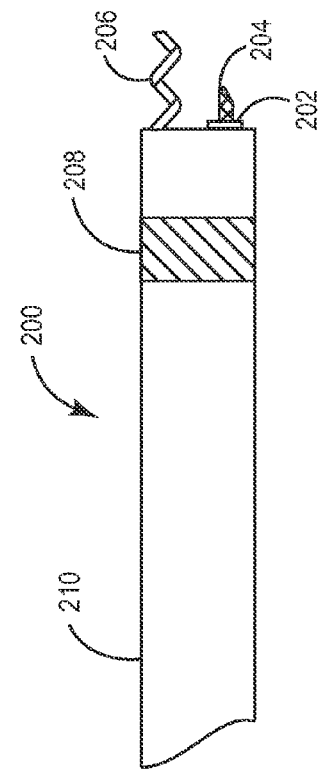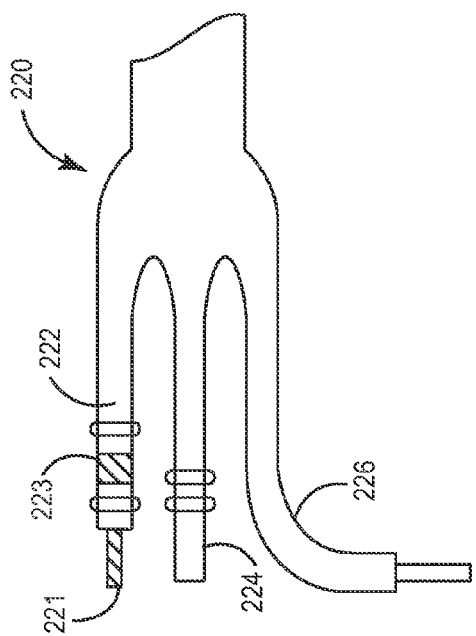

IMPLANTABLE MEDICAL DEVICE HAVING OPTICAL FIBER FOR SENSING ELECTRICAL ACTIVITY

This is a continuation of U.S. patent application Ser. No. 11/676,128, filed on Feb. 16, 2007, (pending), which is incorporated herein by reference.

FIELD OF THE INVENTION

The present invention relates generally to implantable medical devices and, more particularly, the present invention relates to a method and apparatus for sensing an action potential signal of excitable tissue.

BACKGROUND OF THE INVENTION

Medical electrical leads are used in conjunction with numerous types of medical devices for monitoring the electrical activity of and/or stimulating excitable body tissue. Such devices include cardiac pacemakers, cardiac defibrillators, cardioverters, myostimulators, neurostimulators, and other devices for delivering electrical signals to excitable body tissue and/or receiving electrical signals from the tissue. Cardiac rhythm management devices, for example, including pacemakers, cardioverters and defibrillators, are designed to operate so as to sense the intrinsic cardiac electrical activity and deliver appropriately timed electrical stimulation signals when needed, in order to maintain a normal sinus rhythm at a physiological heart rate. The overall performance of these devices depends largely on the performance of the associated lead system.

Medical electrical leads typically bear one or more electrodes located near a distal lead end that is positioned in the vicinity of body tissue targeted for sensing and/or stimulating. An electrical conductor extends between each electrode and a connector provided at the proximal lead end for electrically coupling the lead and its electrode(s) to a medical device. Medical lead conductors are typically insulated, metallic wire based conductors. A number of limitations exist, however, in using medical electrical leads that rely on metallic wire conductors for carrying sensed electrical signals from excitable body tissue to an implanted or external device.

One limitation is the presence of electrical noise, which may be in the form of electromagnetic interference or electrical potential signals arising from other nearby excitable tissue, sometimes referred to as "far-field signals". Such noise or far-field signals contaminate the sensed signal, interfering with the detection of electrical signals of interest. In regard to cardiac rhythm management devices, accurate sensing of intrinsic cardiac events is crucial to device performance. Intrinsic cardiac events of interest can include atrial depolarizations, observed as P-waves on an internal cardiac electrogram (EGM) signal, and ventricular depolarizations, observed as R-waves on an EGM signal. Oversensing or undersensing of these intrinsic events by a cardiac rhythm management device can result in incorrect detection and classification of a rhythm (normal versus pathological), potentially triggering the delivery of unnecessary cardiac stimulation therapy or inappropriately withholding stimulation when it is actually needed.

Inappropriate withholding of cardiac stimulation is undesirable when the patient is pacemaker dependent or the stimulation therapy is life saving. Inappropriate delivery of cardiac stimulation is undesirable because it may cause unnecessary pain to the patient if the therapy delivered is a shock, and can also lead to premature device battery depletion. Moreover, delivery of stimulation therapies in the presence of normal intrinsic cardiac activity can result in stimulation pulses being delivered during the so-called "vulnerable period" of the cardiac cycle, during which cardiac arrhythmias are easily induced in some patients, creating a potentially life-threatening situation.

The vulnerable period immediately follows the repolarization of cardiac cells after a depolarization. The repolarization time of cells located at the stimulation site is difficult to ascertain from EGM signals sensed using metallic wire based leads because EGM signals reflect the summation of many cellular action potential signals as a depolarization wavefront moves through the myocardium. The EGM signal does not resemble an action potential signal and therefore the recovery time of local cells cannot be accurately estimated from an EGM. Moreover, the T-wave, which contains the repolarization information in a far-field EGM, can have complex morphology making it difficult to ascertain exact repolarization time and characteristics using signal processing techniques. To avoid delivering electrical stimulation during the vulnerable period, some stimulation therapies, such as anti-tachycardia pacing therapies, are synchronized with ventricular depolarization and therefore rely on accurate R-wave detection. A more reliable approach to avoiding the vulnerable period, however, would be to sense the local repolarization of cardiac cells at the stimulation site. Therefore it is desirable to provide a medical lead for sensing the entire action potential morphology from which local activation and recovery times can be easily and accurately measured.

To minimize the likelihood of oversensing or undersensing intrinsic cardiac events, special sensing circuitry, such as sense amplifiers having automatically adjustable sensitivity and gain levels and various sense amplifier blanking schemes have been developed. However, despite these improvements, noise and far-field signals remain an infrequent but serious problem that undermines the accuracy of cardiac event sensing using metallic wire based medical electrical leads.

Another limitation encountered with metallic wire based lead systems relates to sensing of an evoked response following a cardiac pacing pulse. During cardiac pacing, evoked response sensing is performed in order to verify that a delivered pacing pulse has depolarized, or "captured," the heart. A pacing threshold search can be performed to determine the minimum pulse energy needed to capture the heart, referred to as the "pacing threshold." During a pacing threshold search, the evoked response is detected following pacing pulses of varying pulse energies in order to determine the pacing threshold. Pacing at a pulse energy just above the pacing threshold (i.e., threshold+a fixed safety margin) is desirable in order to ensure capture while preserving device battery longevity.

During normal pacing operations, capture management schemes typically employ evoked response sensing to verify that capture is not lost due to a change in pacing threshold. False capture detections due to oversensing of noise or far-field signals may result in prolonged episodes of sub-threshold cardiac pacing that is ineffective in maintaining a base heart rate. False loss of capture detections can result from undersensing of the evoked response and can trigger the delivery of unnecessary backup pacing pulses and pacing threshold searches. Increases in pacing pulse energy due to false loss of capture detections can lead to premature pacemaker battery depletion. Accurate capture verification and maintenance of effective cardiac pacing therefore depends on reliable evoked response sensing.

Evoked response sensing using metallic wire based leads is difficult, however, for a number of reasons. A major challenge in evoked response sensing arises due to the post-pace polarization artifact at the electrode-tissue interface. This polarization artifact, also referred to as "afterpotential," can saturate sense amplifiers included in the cardiac pacing device and mask an evoked response signal. Typically, a blanking interval is applied to sense amplifiers during and immediately following a pacing pulse to prevent saturation of the amplifiers. The polarization artifact may diminish during the blanking interval, however, it may still interfere with evoked response sensing. Low-polarization electrodes have been proposed for reducing the polarization artifact. See for example U.S. Pat. No. 4,502,492, issued to Bornzin, or U.S. Pat. No. 6,430,448, issued to Chitre, et al.

Improved methods for performing capture verification based on evoked response sensing using conventional leads have been proposed. Such methods may include special hardware circuitry or special software signal processing methods that reduce or eliminate the problem of polarization artifact. Reference is made to commonly assigned U.S. Pat. No. 6,134,473, issued to Hemming et al. and U.S. Pat. Application No. 20020116031 issued to Vonk.

Selection of separate sensing electrodes for sensing the evoked response, different than the electrode pair used for delivering the pacing pulse, can reduce polarization artifact problems. Other methods proposed for overcoming post-pace polarization artifact during capture verification include sensing a far-field signal related to an evoked response, as opposed to the near-field evoked response signal, or sensing a conducted polarization away from the pacing site. See for example, U.S. Pat. No. 5,324,310 issued to Greeninger, U.S. Pat. No. 5,222,493 issued to Sholder, U.S. Pat. No. 5,331,966 issued to Bennett et al., U.S. Pat. No. 6,434,428 issued to Sloman, et al., and U.S. Pat. App. No. 20010049543, issued to Kroll.

For accurate evoked response detection, however, it is desirable to sense the evoked response in the vicinity of the stimulated cardiac tissue site. Sensing in other areas of the heart could lead to erroneous evoked response detection due to noise or other myopotentials being sensed as an evoked response. Furthermore, sensing for an evoked response conducted to another area of the heart may not be possible in patients having conduction disorders. A medical sensing lead that is not subject to electrical noise, far-field signals or post-pace polarization artifact is therefore desirable for use with cardiac rhythm management devices in order to achieve reliable, accurate sensing of intrinsic and evoked electrical activity.

Accurate sensing of intrinsic electrical activity is important in other diagnostic and therapy delivery applications. Electrophysiological studies are performed on the heart to identify patients that are prone to arrhythmias, and identify and treat arrhythmogenic substrate. Accurate detection of electrical activation and recovery is valuable in understanding the potential for arrhythmias and the pathways by which an arrhythmia originates and is sustained. Therefore, detection of a local action potential signal, rather than a relatively more global EGM signal, would provide more detailed information regarding activation and recovery times of myocardial cells. Detection of local action potential signals would also be valuable in monitoring the effect of pharmaceutical agents on cellular activation and recovery.

In certain cardiac pacing therapies, it is desirable to time the delivery of the pacing pulse relative to myocardial repolarization at the stimulation site. Such therapies include anti-tachycardia pacing, cardiac potentiation therapy based on post-extrasystolic potentiation, and non-excitatory stimulation. During anti-tachycardia pacing, avoiding delivery of a pacing pulse during the vulnerable period is critical in preventing a worsening of the arrhythmia. Detection of approximate local repolarization time based on T-wave sensing is generally disclosed in U.S. Pat. No. 4,593,695 issued to Wittkampf for use in timing the delivery of anti-tachycardia pacing relative to the sensed T-wave.

Post-extrasystolic potentiation (PESP) refers to the enhanced mechanical function of the heart following an early extrasystole. The magnitude of the enhanced mechanical function is strongly dependent on the timing of the extrasystole. Because the extrasystole is most effective just after repolarization, a perceived risk in delivering PESP stimuli is that the extrasystole may fall in the vulnerable period. A post-extra systolic potentiation cardiac pacing stimulator for applying paired or coupled pulses is generally disclosed in U.S. Pat. No. 5,213,098, issued to Bennett et al.

Non-excitatory stimulation (NES) is delivered to cardiac tissue while it is undergoing active depolarization and repolarization to influence electrochemical and electromechanical dynamics in order to modulate cardiac contractility. A method for automatically controlling the delivery of excitable tissue control signals that includes the determination of an estimated action potential duration is generally disclosed in U.S. Pat. No. 6,360,126 issued to Mika et al. The action potential duration is estimated from an action potential related signal which, in a preferred embodiment of the invention, is a close bipolar electrogram signal.

For each of these types of cardiac pacing therapies, therefore, accurate detection of myocardial repolarization would be advantageous in properly timing the delivery of the stimuli. An experimental system for recording high-fidelity transmembrane action potentials using an optical mapping system and voltage-sensitive dye is described by Laurita, et al., Circ. Res. 1996. Methods and apparatus for measuring acute and chronic monophasic action potentials in vivo have been disclosed. Reference is made, for example, to U.S. Pat. No. 4,955,382 issued to Franz et al, U.S. Pat. No. 4,690,155 issued to Hess, U.S. Pat. No. 5,425,363 issued to Wang, and U.S. Pat. No. 6,152,882 issued to Prutchi. These disclosed methods generally include the use of a wire conductor for conducting an electrical signal sensed by a sensing electrode. As indicated above, an electrical signal sensed by a sensing lead or catheter utilizing an electrical wire conductor will generally be subject to electrical noise and artifacts.

Another limitation of metallic wire based leads is that they are generally incompatible with magnetic resonance imaging because the magnetic field can induce unwanted current in metallic wire conductors. In addition, an implanted metallic wire based lead can become dislodged by the strong magnetic field. Because MRI examinations are prescribed for a variety of diagnostic purposes, it is desirable to provide implantable medical sensing leads that are MRI compatible.

BRIEF DESCRIPTION OF THE DRAWINGS

Advantages and features of the present invention will be readily appreciated as the same becomes better understood by reference to the following detailed description when considered in connection with the accompanying drawings, in which like reference numerals designate like parts throughout the figures thereof and wherein:

FIG. 2 is a sectional view of the lead body included in the lead of FIG. 1;

FIG. 3 is a block diagram of excitation/detection circuitry included in the lead system of FIG. 1;

FIG. 4 is a sectional view of a lead body included in an alternative embodiment of an optical fiber based sensing lead system;

FIG. 5 is a block diagram of excitation circuitry included in the alternative system of FIG. 4;

FIG. 10 is a plan view of a combined stimulation and optical fiber based sensing lead system;

FIG. 11 is a sectional view of the distal end of the lead of FIG. 10 illustrating one arrangement of electrical conductors and an optical fiber in a combined stimulating and optical fiber based sensing lead;

DETAILED DESCRIPTION OF THE INVENTION

Figure 1:
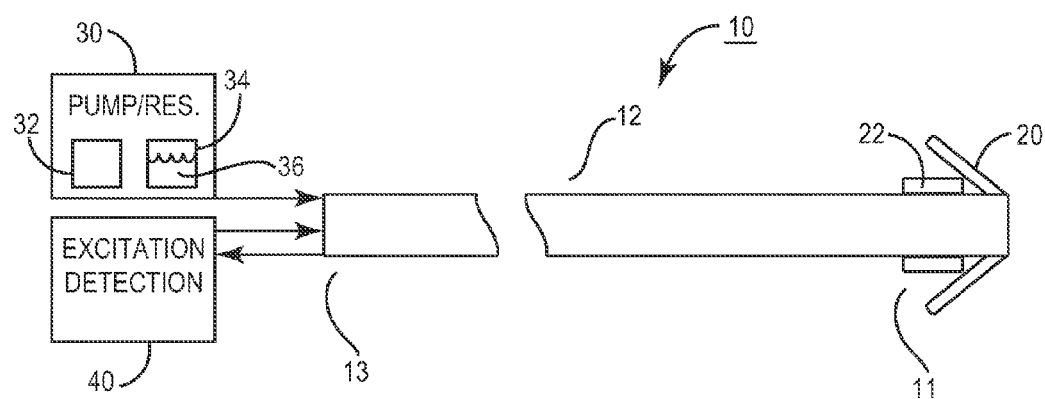
FIG. 1 is a schematic diagram of an optical fiber-based medical lead system for sensing the electrical activity of excitable body tissue either acutely or chronically.

The present invention provides an implantable medical lead for sensing electrical activity of excitable body tissue using an optical fiber for transmitting fluorescence signals associated with the local transmembrane cellular potential changes. The lead is provided with an elongated body carrying at least a first optical fiber extending between a proximal lead end and a distal lead end that is positioned in or against excitable body tissue for monitoring local electrical activity. At the proximal lead end a connector is provided for connecting the lead to an implantable or external monitoring device for acute or chronic monitoring of electrical activity and optionally delivering electrical stimulation or other therapy. Optical excitation and photodetection circuitry are included in a lead connector assembly and/or in the associated medical device. Excitation circuitry includes a light emitting diode positioned relative to the proximal end of the optical fiber to permit emitted light to be passed through an excitation filter and to the distal lead end via the optical fiber. The lead further includes a conduit extending from the proximal lead end to the distal lead end for delivering a controlled amount of a voltage sensitive fluorescence dye to a local, targeted tissue site. Fluctuation in local transmembrane cellular potential will cause changes in the dye's fluorescence intensity. The first or a second optical fiber collects and transmits the fluorescence signal from the distal lead end to the proximal lead end where it is received by detection circuitry. Detection circuitry includes an emission filter and photodetector. The fluorescence signal is converted by the photodetector to an analog electrical signal of the action potential, which may then be digitized and processed to generate an action potential waveform or selected, fiducial points of an action potential waveform.

In one embodiment, the optical fiber is retracted within a hollow needle that can be advanced out of the distal lead end to a desired tissue depth. The optical fiber can then be extended to protrude from the hollow needle to facilitate optical sensing of local electrical activity at a particular region of interest at a depth within the tissue.

Optical sensing of a local action potential has a number of advantages. The fluorescence signal provides a pure signal, not contaminated by extraneous electrical noise or far-field electrical signals. The measured fluorescence signal is directly related to the local activation and recovery of cells in the vicinity of the distal lead end within the volume of released voltage-sensitive dye providing a more specifically localized measurement of tissue activation than ECG and EGM measurements. Localized action potential measurement allows accurate detection and measurement of both activation and recovery times.

These advantages are valuable in a number of monitoring and therapy delivery applications. Electrophysiological mapping studies using an optical fiber based sensing lead are expected to produce accurate, detailed information regarding both local activation and recovery. Mapping studies using an optical fiber based sensing lead may allow easier identification of tissue regions of interest (e.g., bundle of His) based on accurate clear measurement of the electrical properties of the tissue. Monitoring the effects of various pharmaceutical or stimulation therapies is made possible because accurate repolarization information can be obtained from all layers (endocardium to epicardium) of the cardiac tissue that can be differentially affected by such therapies. Such monitoring is useful in adjusting a therapy to achieve a desired effect. Cardiac pacing therapies that rely on accurate stimulation timing relative to myocardial repolarization, such as anti-tachycardia pacing, post-extrasystolic potentiation, and non-excitatory stimulation, could be delivered with greater benefit and less risk. More reliable evoked response sensing and sensing of cardiac intrinsic activity can be achieved using optical fiber based sensing in place of or supplementary to standard EGM sensing, improving the overall performance of cardiac rhythm management devices.

The present invention provides a medical lead that includes one or more optical fibers and associated circuitry for use in sensing the electrical activity of excitable body tissue. Optical sensing of electrical tissue activity allows clear recording of a local action potential signal, thereby providing accurate information regarding the presence and timing of cellular activation and recovery. Such information, especially recovery, can be difficult to determine from metallic wire-based electrical sensing leads because repolarization information is buried in the t-wave, which can have a myriad of complex morphologies. The problem is compounded because of extraneous electrical noise and artifacts that may appear on the electrical signal. Furthermore, optical sensing allows accurate activation and recovery times from a local site as opposed to sensing using a metallic lead that reflects average activation and recovery times from a relatively large region, the size of which depends on the specific electrode configuration (e.g., unipolar versus bipolar).

Because of these advantages, a number of applications may benefit from the use of an optical fiber based sensing lead. Acute electrophysiological studies of the heart or other excitable tissue using optical fiber based sensing leads may provide more accurate diagnostic and mapping information. Mapping of the His bundle location, for example, is desirable for achieving His bundle pacing, which produces ventricular activation that more closely mimics normal physiological activation than pacing at other ventricular sites.

An optical sensing lead is also well-suited for measuring the effects of pharmaceutical or other bioactive agents on cellular excitation and recovery because it has ability to provide complete repolarization information from different layers (endocardium to epicardium) of the myocardium. An optical sensing lead could therefore be used in determining optimal dosages of such agents by monitoring the action potential signal during dosage adjustments until a desired effect is reached.

In chronic cardiac rhythm management applications, accurate sensing of the intrinsic electrical activity is possible without interference due to far-field signals or other noise. More reliable evoked response sensing can be performed using an optical fiber based lead system because post-pace polarization artifacts are not present on the optical signal making capture detection during cardiac pacing more reliable.

Particular cardiac pacing therapies that rely on timing stimulation delivery relative to myocardial repolarization, such as anti-tachycardia pacing, post-extrasystolic potentiation, and non-excitatory stimulation, could be delivered with greater benefit and less risk by accurate measurement of myocardial repolarization using an optical fiber based sensing lead. It is contemplated, therefore, that a medical lead including an optical fiber for sensing action potential signals could be used acutely or chronically for a variety of diagnostic or therapy delivery applications.

FIG. 1 is a schematic diagram of an optical fiber-based medical lead system for sensing the electrical activity of excitable body tissue either acutely or chronically. Lead 10 includes an elongated lead body 12, extending between a distal end 11 and a proximal end 13. Distal end 11 is positioned in or against excitable tissue, such as myocardium, smooth or skeletal muscle, or nerve tissue. A fixation member 20 is provided for stabilizing the lead position at a desired location. Fixation member 20 is shown in FIG. 1 as a fixation tine, which is known for use in endocardial leads. The fixation tine engages the ventricular trabeculae, preventing dislodgment and shifting of the distal lead end. Alternative fixation mechanisms may be used such as hooks, barbs, helices, suction, etc., for stabilizing distal end 11 at a targeted tissue sensing site.

For chronic use, a drug-eluting member 22 is provided near distal lead end 11. Drug-eluting member 22 preferably elutes a glucocorticosteroid, such as a water-soluble salt of dexamethasone, to minimize encapsulation of the distal lead end. Collagenous tissue capsule formation around lead 10 due to the foreign body response is preferably reduced or minimized in order to minimize the attenuation of light transmission between an optical fiber carried by lead 10 and the adjacent excitable tissue and to prevent alteration of the local action potential signal. Drug-eluting member 22 may take the form of an annular monolithic controlled release device, similar to that implemented commercially by Medtronic, Inc. in the Model 5534 Capsure Z™ lead. For details regarding drug-eluting leads for reducing or minimizing encapsulation due to the foreign body response, general reference is made to U.S. Pat. No. 4,506,680 issued to Stokes, incorporated herein by reference in its entirety.

Lead body 12 is provided for carrying at least one optical fiber and a conduit for carrying a voltage-sensitive fluorescent dye between proximal lead end 13 and distal lead end 11. As such, proximal lead end 13 communicates with a dye-dispensing device 30, which includes a pumping mechanism 32 and a reservoir 34 for storing a voltage-sensitive fluorescent dye 36. Proximal lead end 13 is additionally coupled to excitation/detection circuitry 40. Excitation/detection circuitry 40 sends and receives light transmitted via an optical fiber carried by lead body 12 to and from distal lead end 11. Excitation and detection circuitry 40 may be entirely or partially included in a proximal connector assembly on lead 10 or in an associated implantable or external device coupled to lead 10 for monitoring action potential signals.

FIG. 2 is a sectional view of lead body 12 included in lead 10 of FIG. 1. Lead body 12 is provided as a tubular member for carrying a conduit 16 and an optical fiber 18. Lead body 12 is formed from a biocompatible polymeric material, such as polyurethane, known for use in medical leads.

Conduit 16 is provided for carrying a voltage-sensitive fluorescent dye 36 from dye-dispensing device 30 to excitable tissue adjacent to distal lead end 11. A controlled amount of dye 36 is released from reservoir 34 into the surrounding tissue, under the control of dye-dispensing device 20, such that when the tissue is exposed to excitation light, the released dye will fluoresce with an intensity that varies as the cellular transmembrane potential in the surrounding, dye-exposed tissue varies. Examples of appropriate dyes that can be used in conjunction with the present invention are di-4-ANEPPS, di-8-ANEPPS and RH237 available from Molecular Probes, Eugene, Oreg. Dye-dispensing device 20 may be provided as an implantable fluid pump or other fluid dispensing mechanism capable of releasing controlled amounts of fluid. The volume of dye released is controllable and at any given time the dye released is sufficient to stain the tissue directly beneath the fiber to an extent that the fluorescence signal is maximized.

Lead body 12 further includes an optical fiber 18 for transmitting light signals between proximal and distal lead ends 13 and 11. Optical fiber 18 may be provided as a commercially available optical fiber formed from glass or plastic. Optical fiber 18 is preferably of a relatively small diameter, for example on the order of 0.5 to 1.5 mm.

FIG. 3 is a block diagram of excitation/detection circuitry included in lead 10 of FIG. 1. A light-emitting diode (LED) 42 emits light, typically green light, which is filtered through excitation filter 44 to eliminate other, extraneous light wavelengths. The filtered excitation light 48, indicated by dashed arrow, is directed by a dichroic mirror 46 into optical fiber 18. Dichroic mirror 48 is designed to reflect light having the primary wavelength emitted by LED 42. The excitation light 48 is transmitted via optical fiber 18 to excitable tissue adjacent distal end 11 of lead 10. Green light emitted into the surrounding tissue will provide the excitation energy needed for a voltage-sensitive dye to fluoresce. As surrounding cells are depolarized and repolarized, the fluorescence intensity will vary to reflect the changes in the transmembrane potential during an action potential.

The fluorescence signal is transmitted via optical fiber 18 from distal end 11 to proximal end 13 of lead 10 where the signal is collected by excitation/detection circuitry 40. Dichroic mirror 46 is designed to pass light having a wavelength corresponding to the primary wavelength of the fluorescence signal, typically red light. The fluorescence signal 54, indicated by solid arrow, is thus transmitted through dichroic mirror 46 to emission filter 50. Dichroic mirror 46 thus acts to separate the excitation and fluorescence light signals. Because dichroic mirror 46 may pass some extraneous light (e.g., green light used for excitation), emission filter 50 is provided to further filter the fluorescence light. Detection circuitry 52 receives the filtered, fluorescence light. If the separation of excitation and fluorescence light by dichroic mirror 46 is adequate, inclusion of excitation and emission filters 44 and 50 in excitation/detection circuitry 40 is optional. Detection circuitry 52 generally includes a photodetector for converting the light signal into an electrical signal and an amplifier for amplifying the electrical signal output to be received by signal processing circuitry of an associated device.

FIG. 4 is a sectional view of a lead body included in an alternative embodiment of an optical fiber based sensing lead. In this embodiment, lead body 12 includes a first optical fiber 80 for transmitting excitation light to the distal lead end and a second optical fiber 70 for transmitting the fluorescence light signal to the proximal lead end. Optical fiber 80 is coupled to excitation circuitry 82, and optical fiber 70 is coupled to detection circuitry 72.

As shown in FIG. 5, excitation circuitry 82 includes an LED 84 and an excitation filter 86 for producing a pure excitation light signal 88 for transmission via optical fiber 80 to the distal lead end. Detection circuitry 72 includes an emission filter 76 for receiving the fluorescence light signal 78 and providing a pure, fluorescence light signal to detection circuitry 74.

In order to avoid light signal loss due to misalignment of the optical fiber 70 with photodetector 74, photodetector 74 may be provided with a surface relatively larger than the diameter of optical fiber 70. Photodetector 74 will thereby continue to receive transmitted light from optical fiber 70 despite alignment shifts. However, a design tradeoff will be made in selecting the size of photodetector 74 relative to optical fiber 70 in that the signal-to-noise ratio may worsen as the size of photodetector 74 is increased.

Figure 6:
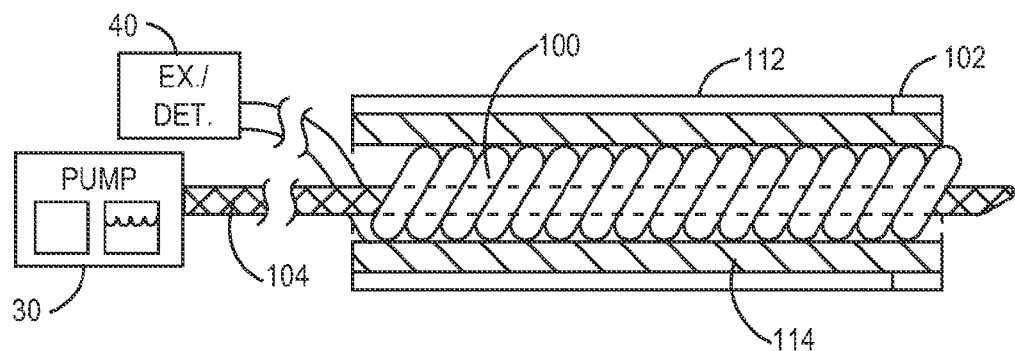
FIG. 6 is a sectional view of one embodiment of an optical fiber based sensing lead in which an optical fiber is provided in the shape of a helical coil.

FIG. 6 is a sectional view of one embodiment of an optical fiber based sensing lead in which an optical fiber is provided in the shape of a helical coil. Optical fiber 100 is formed as a helical coil having a pitch and diameter designed to avoid bending optical fiber 100 beyond its critical radius. Fiber 100 is preferably wound on a central support 104, which can additionally serves as a conduit for delivering the fluorescent dye. The embodiment shown in FIG. 6 is expected to improve the reliability of an optical fiber based sensing lead by improving the mechanical stability of the fiber through a helical coil design. The helical coil design ensures that bending of the fiber beyond its critical radius does not occur during lead deployment, which would otherwise result in a loss of signal.

The embodiment shown in FIG. 6 further includes a distal sealing member 102 provided for preventing the ingress of blood or other bodily fluids into the distal end of lead body 112. The ingress of bodily fluids into a medical lead is generally undesirable because infection can develop. With regard to a fiber optic based sensing lead, blood migration to the proximal lead end could contaminate the transmission of a light signal between the optical fiber and the detection circuitry interface. In FIG. 6, sealing member 102 is provided as an annular band that can be tightened, by crimping, for example, to compress an inner wall of lead body 112 against optical fiber 100 and thereby create a fluid-tight seal between the inner diameter of lead body 112 and the outer diameter of optical fiber 100.

Figure 7:
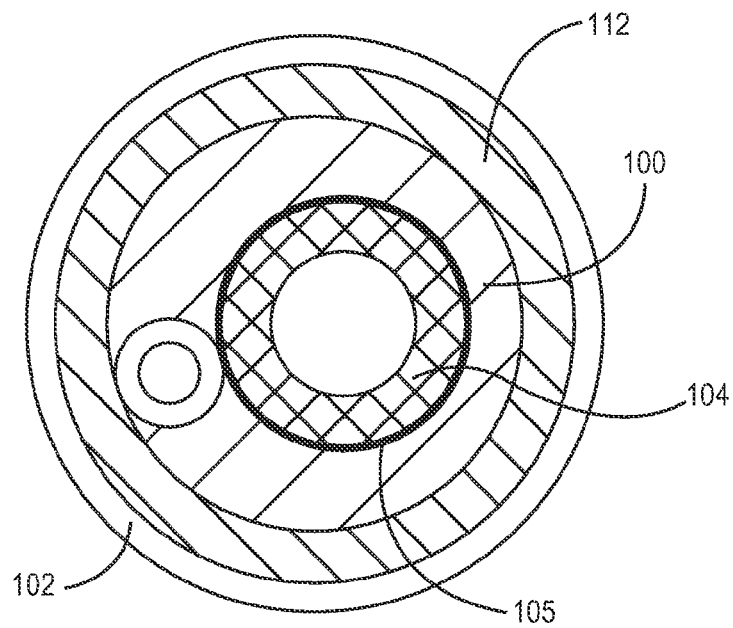
FIG. 7 is an end view of the lead of FIG. 6.

FIG. 7 is an end view of the lead of FIG. 6. Helically wound optical fiber 100 forms a central lumen in which a hollow supporting core 104 resides and additionally serves as a dye conduit. Annular sealing member 102 is tightened around a resilient outer lead body 112 to form a fluid tight seal between lead body 112 and optical fiber 100. The outer diameter of optical fiber 100 may be coated (not shown) such that grooves between turns of the helix are filled producing a smooth outer diameter for forming a seal with the inner diameter of lead body 112. An additional gasket or sealing device 105 may be provided between the inner diameter of optical fiber 100 and the outer diameter of core 104.

Other methods for sealing the distal end of a medical lead against the ingress of body fluids may be adapted for use with the present invention. A sealing membrane within the lumen of a distal lead tip is generally disclosed in U.S. Pat. No. 4,311,153 issued to Smits. Another method for sealing the lumen of a medical lead is generally disclosed in U.S. Pat. No. 5,948,015 to Hess et al.

Figure 8:
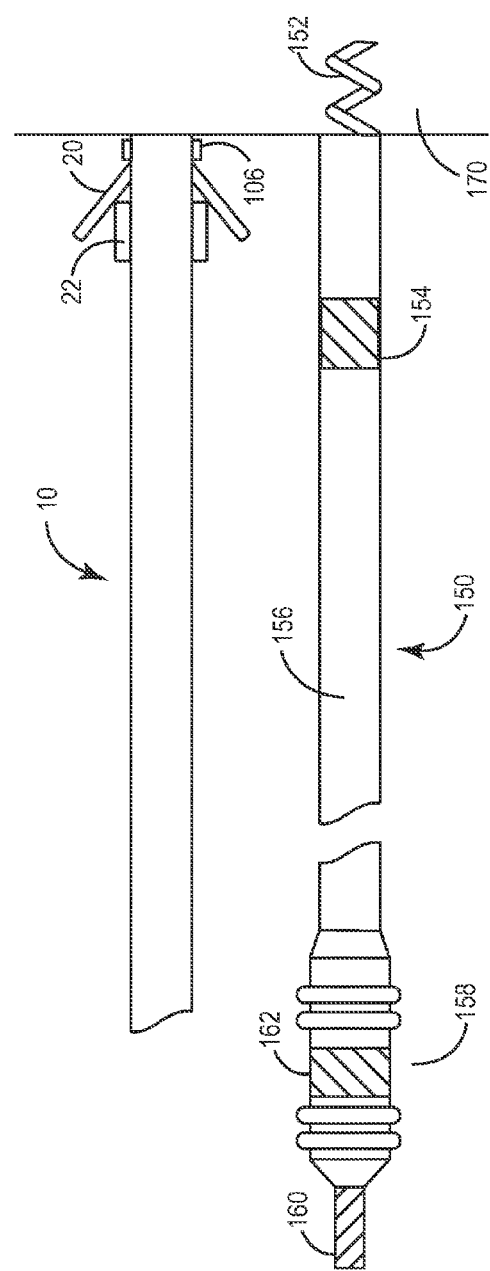
FIG. 8 is a plan view of an optical fiber based sensing lead positioned against myocardial tissue, adjacent a cardiac pacing lead.

FIG. 8 is a plan view of an optical fiber based sensing lead positioned against myocardial tissue, adjacent a cardiac pacing lead. Cardiac pacing lead 150 is depicted as an exemplary bipolar, active fixation pacing lead having a distal tip electrode 152, shown as a fixation helix, a ring electrode 154 positioned proximal tip electrode 152 and a lead body 156 for carrying conductors between tip and ring electrodes 152 and 154 and a proximal connector assembly 158 for enabling electrical connection to a cardiac pacing device. Sensing lead 10 is positioned for sensing action potential signals in the myocardial tissue 170. Sensed action potential signals may be associated with passing intrinsic depolarization wave fronts or evoked depolarization wave fronts due to delivery of an electrical impulse by pacing lead 150.

Figure 9:
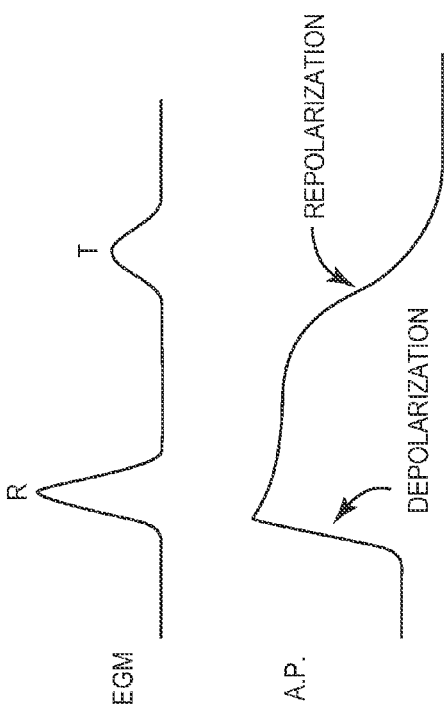
FIG. 9 is an illustration of a representative EGM signal and an action potential (AP) signal of the type that may be recorded from an optical sensing lead.

FIG. 9 is an illustration of a representative EGM signal that may be sensed by the cardiac pacing lead of FIG. 8 and an action potential (AP) signal of the type that may be recorded from an optical fiber based sensing lead. The R-wave on the EGM signal corresponds to activation of the ventricular myocardium and approximately coincides with the sharp rise of an action potential signal indicating depolarization of myocardial cells. The EGM T-wave corresponds to recovery of the ventricular myocardium and approximately coincides with the fall of the action potential signal indicating repolarization of myocardial cells. The EGM signal is a relatively global signal, representing the summation of the transmembrane potential changes from a myocardial mass, the size of which depends on the electrode configuration. The EGM signal may not be specific enough to accurately measure time of activation and recovery of local cardiac cells, especially when the source of EGM signal is a far-field vector. Local activation and recovery time can be easily measured from the action potential signal received from an optical fiber based lead.

FIG. 10 is a plan view of a combined stimulation and optical fiber based sensing lead. Lead 200 includes a helically coiled optical fiber 202, a dye-delivery conduit 204 extending through the lumen formed by the helically coiled optical fiber 202, a tip electrode 206 and a ring electrode 208. A lead body 210 is provided for carrying wire conductors associated with the tip and ring electrodes 206 and 208 and the optical fiber 202 and dye-delivery conduit 204 between the distal and proximal ends of lead 200. While a particular bipolar stimulation electrode arrangement is shown, it is recognized that unipolar, bipolar or multipolar electrode arrangements are possible using various combinations of tip, ring, coil, or other types of electrodes known for use in medical electrical leads.

Lead 200 is provided with a proximal, trifurcated connector assembly 220. Connector branch 222 includes a pin connector 221 and a ring connector 223 for providing electrical connection between tip and ring electrodes 206 and 208, respectively, to an associated medical device. Connector branch 224 is provided for coupling optical fiber 202 to an associated medical device containing excitation and photodetection circuitry for action potential sensing. In an alternative embodiment, excitation and/or photodetection circuitry are included within connector assembly 220. When excitation and/or photodetection circuitry are included within connector assembly 220, appropriate electrical connectors are provided on connector branch 224 for conducting current needed for energizing excitation circuitry and for conducting the electrical signal output from photodetection circuitry to input circuitry of an associated medical device. Connector branch 226 is provided for connecting conduit 204 to a fluid dispensing device containing a voltage sensitive fluorescent dye.

FIG. 11 is a sectional view of the distal end of lead 200 of FIG. 10 illustrating one arrangement of electrical conductors and an optical fiber in a combined stimulating and optical fiber based sensing lead, according to the present invention. A coiled electrical conductor 212 is provided as a multifilar conductor wherein an individually insulated filar is provided for electrical connection to ring electrode 208 and another individually insulated filar is provided for connecting to tip electrode 206. In alternative embodiments, individual wire conductors for providing electrical connection to tip and ring electrodes 206 and 208 may be provided as stranded, cabled conductors, straight wire conductors, or other conductor types known for use in medical electrical leads.

In FIGS. 10 and 11, the combined stimulating and optical fiber based sensing lead is shown having a single optical fiber for transmitting excitation light and a fluorescence signal. A combined stimulating and optical fiber based sensing lead could also employ two optical fibers for separately transmitting excitation light and collecting fluorescence signal as described previously in conjunction with FIGS. 4 and 5.

Figure 12A:
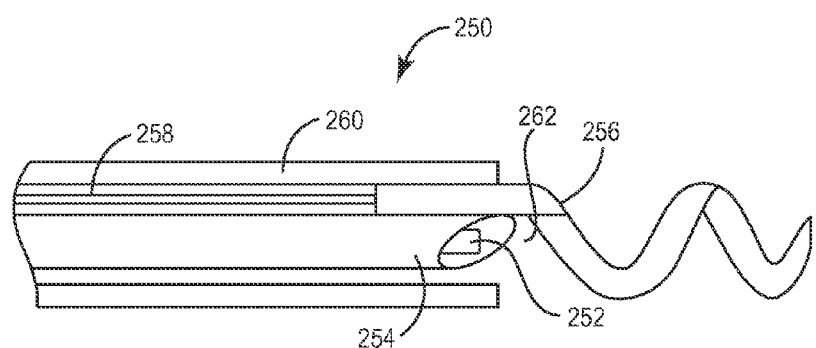
FIG. 12A is a cut-away view of the distal end of an alternative embodiment of an optical fiber based sensing lead.

FIG. 12A is a cut-away plan view of the distal end of an alternative embodiment of an optical fiber based sensing lead. Lead 250 includes an optical fiber 252 carried in the lumen of a hollow needle 254. Needle 254 may be retracted or advanced relative to the lead body 260. Thus, needle 254 can be extended out the opening 262 of the distal end of lead 250 from a retracted position of FIG. 12A to an advanced position of FIG. 12B, and vice versa. A fixation member 256 is provided for anchoring the distal lead end at a desired tissue site. Fixation member 256 is shown in the form of a fixation helix but could alternatively take the form of a barb, hook, suction or other fixation mechanism. With regard to the embodiment shown in FIGS. 12A and 12B, needle 254 is coaxial with fixation helix 256 allowing needle 254 to be extended through helix 256 such that after helix 256 is fixed in tissue, needle 254 can be extended to penetrate the tissue to a desired depth.

Optical fiber 252 is preferably extendable and retractable with respect to needle 254 such that when needle 254 is advanced into a tissue site, optical fiber 252 remains retracted within needle 254 to prevent damage to the tip of the optical fiber 252. Optical fiber 252 may then be advanced flush with the distal tip of needle 254 or extend partially out of needle 254 to allow optical sensing of tissue activity. A voltage-sensitive dye is delivered locally to the tissue via needle 254 or a separate conduit (not shown) provided for dye delivery as described previously. Needle 254 may be advanced in a stepwise manner allowing action potential measurements to be made at different tissue depths. A final fixed position of needle 254 and optical fiber 252 can be selected based on observing action potential signals at varying depths.

Figure 12B:
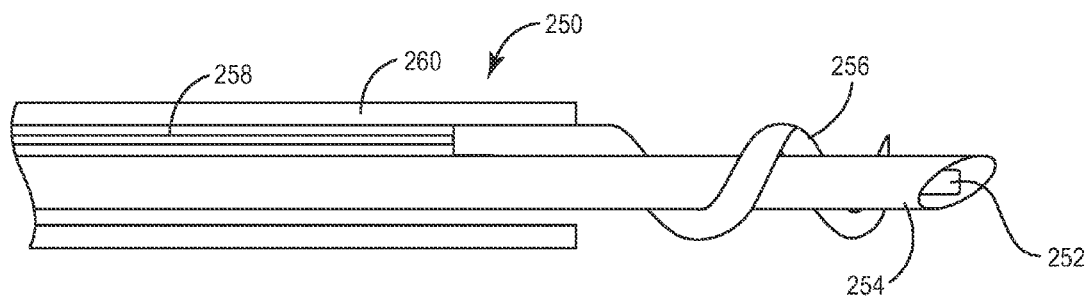
FIG. 12B is a cut-away view of the distal end the lead of FIG. 12A showing an extendable needle in an advanced position.
Figure 13:
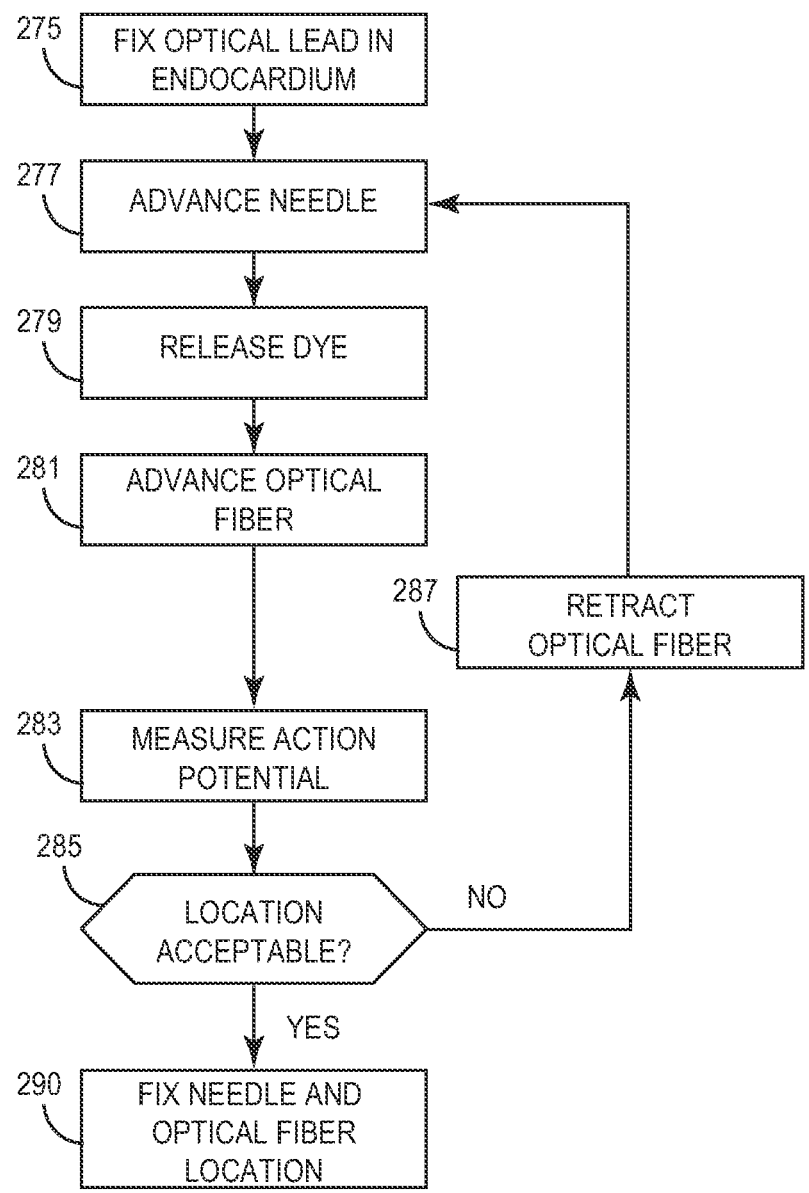
FIG. 13 is a flow chart summarizing a method for using the extendable optical sensing lead of FIGS. 12A and 12B.

FIG. 13 is a flow chart summarizing a method for using the extendable optical sensing lead of FIGS. 12A and 12B. In some applications, it may be desirable to measure electrical activity at a particular depth within a tissue. For example, myocardial cells situated in the deeper layers of the myocardium (known as "m-cells") have different electrical properties, characterized by a prolonged action potential, compared to cells located in the endocardial or epicardial layers. Certain drugs, such as some potassium ion blocking drugs, act differently on these deeper myocardial cells compared to endocardial and epicardial cells. Therefore, positioning an optical fiber based sensing lead within these deeper layers to monitor local electrical activity would be advantageous in monitoring the effects of such drugs and optimizing drug dosages. In the case of potassium ion blocking drugs, monitoring the action potential duration in these different layers using an optical fiber based lead could be performed during drug titration. A fairly uniform distribution of action potential durations through the myocardial layers would suggest that the drug is having its desired effect.

At step 275 of FIG. 13, the distal end of the optical lead 250 is fixed at a selected tissue site, for example on the endocardium, using distal fixation member 256. During advancement of lead 250 to the tissue site, hollow needle 254 remains retracted within lead body 260 to prevent tissue damage. At step 277, needle 254 is advanced out of the distal lead end 262 to penetrate the tissue to a desired depth. At step 279, a controlled amount of a voltage sensitive dye is released either through needle 254 or a separate conduit (not shown in FIG. 12) into the surrounding tissue. At step 281, optical fiber 252 residing within hollow needle 254 is advanced until it protrudes form the needle 254 such that it is in contact with surrounding excitable tissue. Optical fiber 252 up to this point has remained within needle 254 to prevent damage to the fiber tip. At step 283 of FIG. 13, the local action potential signal is measured.

At decision step 285, the local action potential signal is evaluated to determine if the measured signal is representative of the electrical properties of the tissue region of interest. If not, optical fiber 252 is retracted slightly at step 287 allowing needle 254 to be advanced again at step 277. Steps 279 through 285 are repeated for each stepwise advancement (step 277) of needle 254 until optical 254 fiber is positioned in the tissue region of interest as evidenced by the measured electrical activity. For example, the deeper layers of the myocardium can be identified by detecting a prolonged action potential signal as the needle is advanced from the endocardial layers deeper into the myocardium. At step 290 the needle and optical fiber positions are fixed to allow electrical activity sensing at the selected tissue depth.

Figure 14:
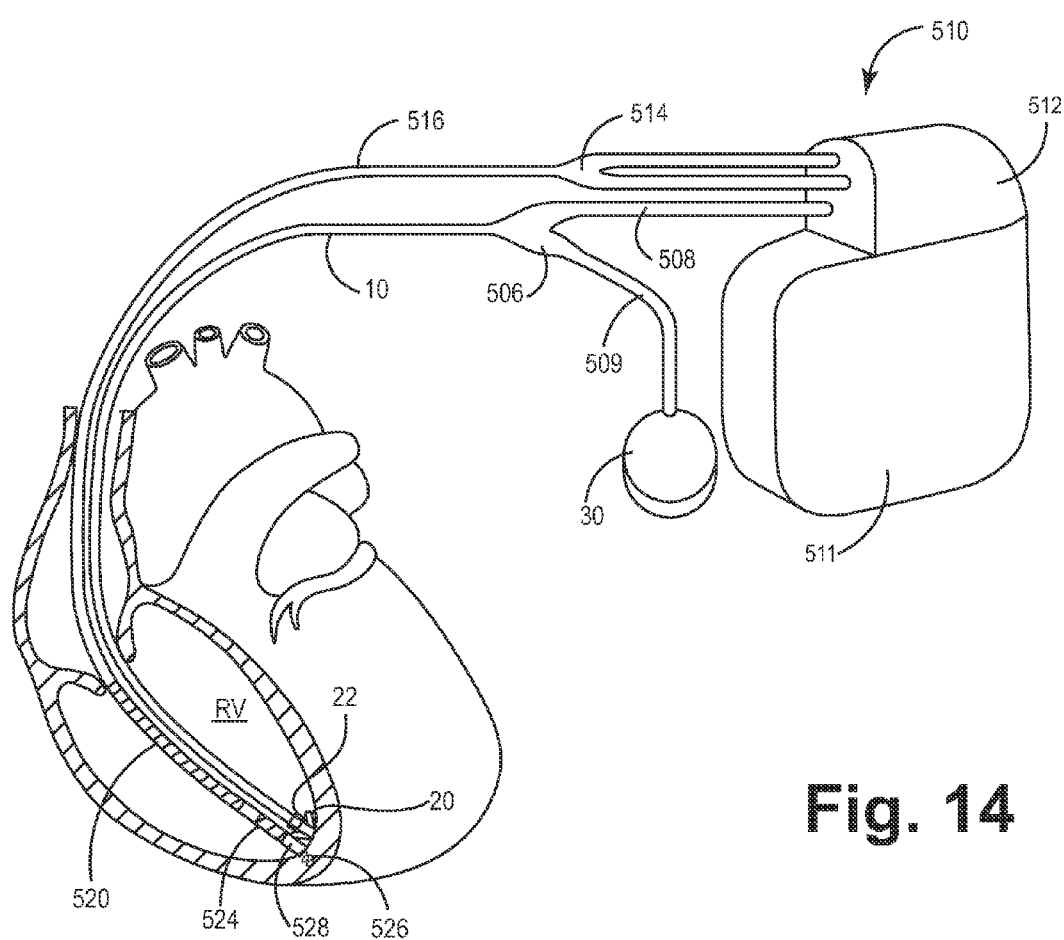
FIG. 14 is a partially cut-away view of a patient's heart coupled to an implantable medical device by way of an electrical stimulation and sensing lead and an optical fiber based sensing lead.

As noted previously, an optical fiber sensing lead could be used in conjunction with cardiac rhythm management devices to improve sensing of intrinsic and evoked cardiac electrical activity. FIG. 14 is a partially cut-away view of a patient's heart coupled to an implantable medical device by way of an electrical stimulation and sensing lead and an optical fiber based sensing lead. The implantable medical device (IMD) 510 is an exemplary cardiac rhythm management device capable of delivering cardiac pacing, cardioversion, and defibrillation therapies, sensing EGM signals and, in accordance with the present invention, sensing action potential signals received from optical fiber based sensing lead 10.

IMD 510 includes a connector block 512 for receiving the proximal end of a right ventricular electrical lead 516 and the proximal end of optical fiber based sensing lead 10. Right ventricular lead 516 is positioned such that its distal end is in the vicinity of the right ventricle for sensing right ventricular EGM signals and delivering pacing or shocking pulses in the right ventricle. For these purposes, right ventricular lead 516 is equipped with a ring electrode 524, an extendable helix electrode 526 mounted retractably within an electrode head 528, and a coil electrode 520, each of which are connected to an insulated conductor within the body of lead 516. The proximal end of the insulated conductors are coupled to corresponding connectors carried by bifurcated connector 514 at the proximal end of lead 516 for providing electrical connection to the IMD 510.

The tip and ring electrodes 524 and 526 may be used as a bipolar pair, commonly referred to as a "tip-to-ring" configuration, or individually in a unipolar configuration with the device housing 511 serving as the indifferent electrode, commonly referred to as the "can" or "case" electrode. The device housing 511 may also serve as a subcutaneous defibrillation electrode in combination with coil electrodes 520 for defibrillation of the ventricles.

Optical sensing lead 10 corresponds to the lead shown in FIG. 1. Optical lead 10 includes fixation member 20 and drug-eluting member 22. Lead 10 is shown in FIG. 14 having a proximal bifurcated connector assembly 506. Connector branch 508 is connected to connector block 512 of IMD 510 to provide optical coupling of the optical fiber within lead 10 to excitation and detection circuitry within IMD 510. Connector branch 509 connects the conduit within lead 10 to a fluid-dispensing device 30 containing a voltage-sensitive fluorescent dye.

It is recognized that alternate lead systems may be substituted for the two lead system illustrated in FIG. 14. Other types of electrical stimulation leads may be substituted for right ventricular lead 516 which may include unipolar, bipolar or multipolar combinations of a tip electrode, one or more ring electrodes and/or one or more defibrillation coil electrodes. Alternatively, a combined electrical stimulation and optical fiber-based sensing lead, such as lead 200 of FIG. 10, for example, may be substituted for the two separate leads shown in FIG. 14.

Although IMD 510 is shown coupled to an electrical stimulation lead and an optical fiber-based sensing lead positioned in only one heart chamber, it is understood that the use of an optical fiber based sensing lead or combined electrical stimulation and optical fiber based sensing lead may be expanded to two, three, or all four heart chambers by positioning additional leads in the vicinity of the right atrium, left ventricle and/or left atrium as desired.

Figure 15:
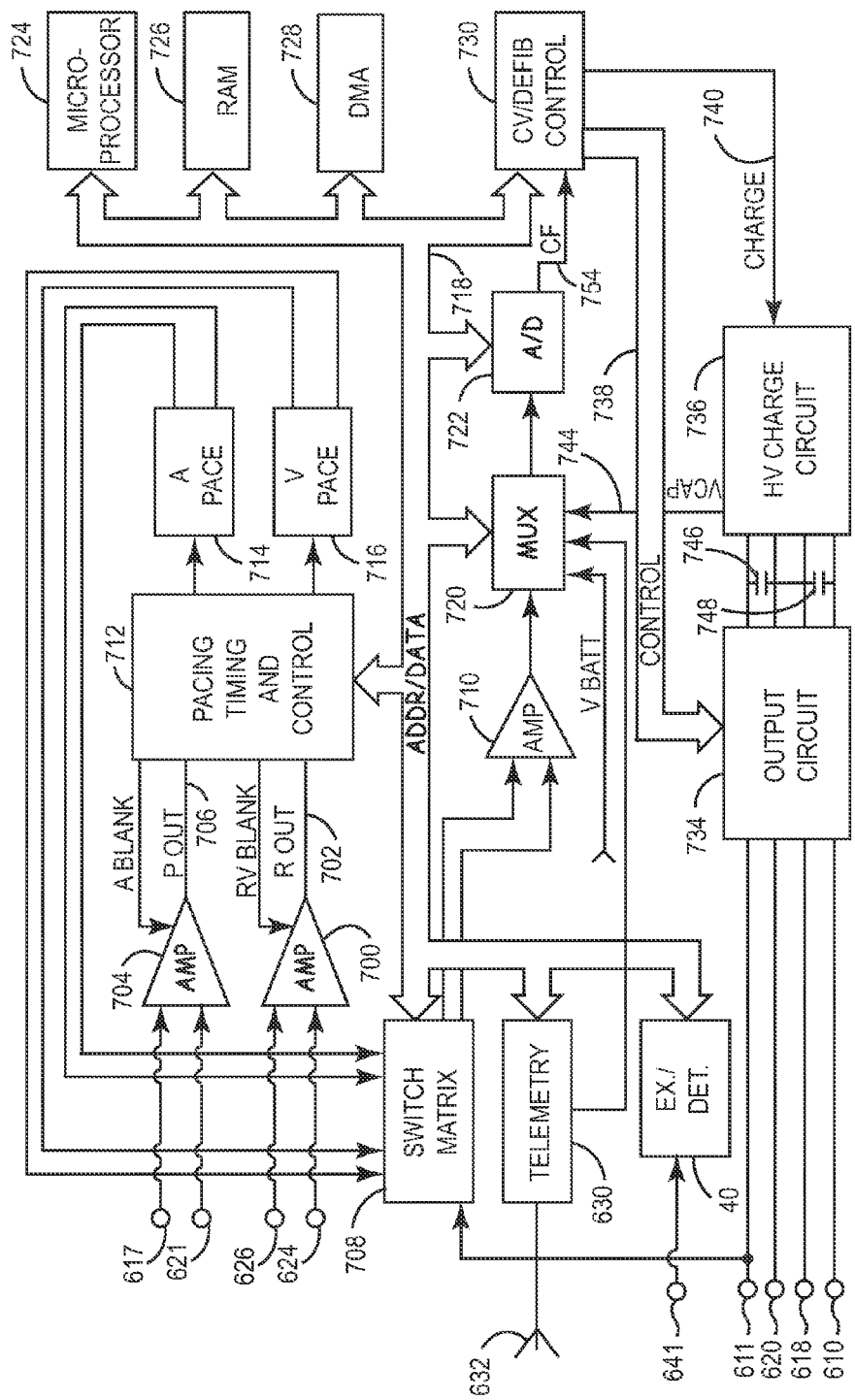
FIG. 15 is a functional schematic diagram of the implantable medical device of FIG. 14.

A functional schematic diagram of IMD 510 is shown in FIG. 15. This diagram should be taken as exemplary of the type of device in which the invention may be embodied and not as limiting. The disclosed embodiment shown in FIG. 15 is a microprocessor-controlled device, but the methods of the present invention may also be practiced in other types of devices such as those employing dedicated digital circuitry.

IMD 510 is provided with a number of electrical connection terminals for achieving electrical connection to associated electrical stimulation and EGM sensing leads. With regard to the system shown in FIG. 14, connection terminal 611 provides electrical connection to the housing 511 for use as the indifferent electrode during unipolar stimulation or sensing. The connection terminals 620 provides electrical connection to coil electrode 520. Each of these connection terminals 611 and 620 are coupled to high voltage output circuit 734 to facilitate the delivery of high-energy shocking pulses to the heart using coil electrodes 520 housing 511. Additional connection terminals 618 and 610 are available for use with other lead systems that include additional high-voltage coil electrodes which may be positioned on additional leads positioned in the right atrium on a right atrial lead or in the vicinity of the left atrium or left ventricle on a coronary sinus lead.

Connection terminals 626 and 624 provide electrical connection to the helix electrode 526 and the ring electrode 524 positioned in the right ventricle. Connection terminals 626 and 624 are further coupled to a ventricular sense amplifier 700 for sensing ventricular signals. Additional connection terminals 617 and 621 are illustrated to facilitate additional electrical connections to additional electrodes that may be present in alternate lead systems which include a right atrial lead bearing a tip electrode and ring electrode for atrial EGM sensing and stimulation.

An optical fiber connection terminal 641 is provided for coupling an optical fiber included in optical fiber sensing lead 10 to excitation and detection circuitry 40, described previously in conjunction with FIG. 3. Additional optical fiber connection terminals and associated excitation and detection circuits may be provided as needed for coupling additional leads including an optical fiber for sensing action potential signals. Excitation and detection circuit 40 provides output to and receives controlling signals from microprocessor 724 via address/data bus 718.

Fluorescence signals received from lead 10 are converted to analog signals by a photodetector included in excitation and detection circuitry 40 which are then digitized by A/D converter 722 and subsequently processed by microprocessor 724 for generating an action potential waveform or points along an action potential waveform for use in detecting and characterizing local myocardial depolarization and/or repolarization.

The atrial sense amplifier 704 and the ventricular sense amplifier 700 preferably take the form of automatic gain controlled amplifiers with adjustable sensing thresholds as is known in the art of cardiac pacing. Whenever a signal received by atrial sense amplifier 704 exceeds an atrial sensing threshold, a signal is generated on the P-out signal line 706. Whenever a signal received by the ventricular sense amplifier 700 exceeds a ventricular sensing threshold, a signal is generated on the R-out signal line 702.

Switch matrix 708 is used to select which of the available electrodes are coupled to a wide band amplifier 710 for use in digital signal analysis. Selection of the electrodes is controlled by the microprocessor 724 via data/address bus 718. The selected electrode configuration may be varied as desired for the various sensing, pacing, cardioversion and defibrillation functions of the IMD 510. Signals from the electrodes selected for coupling to bandpass amplifier 710 are provided to multiplexer 720, and thereafter converted to multi-bit digital signals by A/D converter 722, for storage in random access memory 726 under control of direct memory access circuit 728. Microprocessor 724 may employ digital signal analysis techniques to characterize the digitized signals stored in random access memory 726 to recognize and classify the patient's heart rhythm employing any of the numerous signal processing methodologies known in the art.

The telemetry circuit 630 receives downlink telemetry from and sends uplink telemetry to other implanted or external devices, such as an external programmer as is conventional in implantable cardiac rhythm management devices, by means of an antenna 632. Data for uplink telemetry and control signals for the telemetry circuit are provided by microprocessor 724 via address/data bus 718. Received telemetry is provided to microprocessor 724 via multiplexer 720. Numerous types of telemetry systems known for use in implantable devices may be used. With regard to the system shown in FIG. 14, telemetry commands may be uplinked to implanted dye-dispensing device 30 to control when and/or how much of dye is released.

The remainder of the circuitry illustrated in FIG. 15 is an exemplary embodiment of circuitry dedicated to providing cardiac pacing, cardioversion and defibrillation therapies. The pacer timing and control circuitry 712 includes programmable digital counters which control the basic time intervals associated with various single, dual or multi-chamber pacing modes or anti-tachycardia pacing therapies delivered in the atria or ventricles. Pacer circuitry 712 also determines the amplitude of the cardiac pacing pulses under the control of microprocessor 724.

During pacing, escape interval counters within pacer timing and control circuitry 712 are reset upon sensing of R-waves or P-waves as indicated by signals on lines 702 and 706, respectively. In accordance with the selected mode of pacing, pacing pulses are generated by atrial pacer output circuit 714 and ventricular pacer output circuit 716. The pacer output circuits 714 and 716 are coupled to the desired electrodes for pacing via switch matrix 708. The escape interval counters are reset upon generation of pacing pulses, and thereby control the basic timing of cardiac pacing functions, including anti-tachycardia pacing.

The durations of the escape intervals are determined by microprocessor 724 via data/address bus 718. The value of the count present in the escape interval counters when reset by sensed R-waves or P-waves can be used to measure R-R intervals and P-P intervals for detecting the occurrence of a variety of arrhythmias.

The microprocessor 724 includes associated ROM in which stored programs controlling the operation of the microprocessor 724 reside. A portion of the memory 726 may be configured as a number of recirculating buffers capable of holding a series of measured intervals for analysis by the microprocessor 724 for predicting or diagnosing an arrhythmia.

In response to the detection of tachycardia, anti-tachycardia pacing therapy can be delivered by loading a regimen from microcontroller 724 into the pacer timing and control circuitry 712 according to the type of tachycardia detected. In the event that higher voltage cardioversion or defibrillation pulses are required, microprocessor 724 activates the cardioversion and defibrillation control circuitry 730 to initiate charging of the high voltage capacitors 746 and 748 via charging circuit 736 under the control of high voltage charging control line 740. The voltage on the high voltage capacitors is monitored via a voltage capacitor (VCAP) line 744, which is passed through the multiplexer 720. When the voltage reaches a predetermined value set by microprocessor 724, a logic signal is generated on the capacitor full (CF) line 754, terminating charging. The defibrillation or cardioversion pulse is delivered to the heart under the control of the pacer timing and control circuitry 712 by an output circuit 734 via a control bus 738. The output circuit 734 determines the electrodes used for delivering the cardioversion or defibrillation pulse and the pulse wave shape.

In operation, output from excitation and detection circuit 40 is used in cardiac pacing applications for detecting intrinsic depolarizations, detecting evoked depolarizations following a pacing pulse, and/or for verifying the presence or absence of cardiac electrical activity based on EGM signal sensing.

Figure 16:
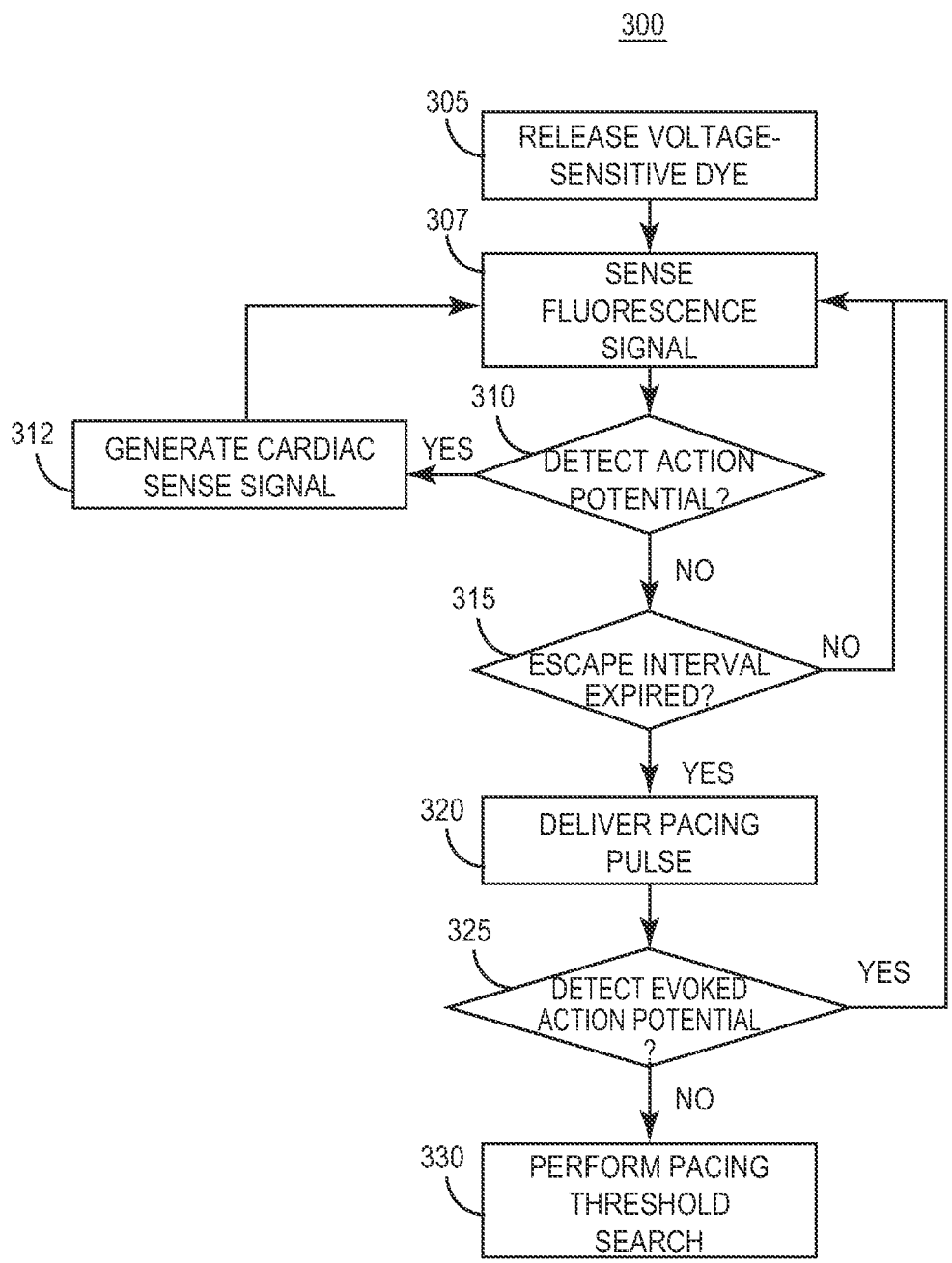
FIG. 16 is a flow chart summarizing one method for using an optical fiber based sensing lead in conjunction with a cardiac pacing device, such as the device of FIG. 15.

FIG. 16 is a flow chart summarizing a method for using an optical fiber based sensing lead according to the present invention. At step 305, once the optical fiber has been properly position in the tissue, a voltage-sensitive dye is released into tissue adjacent the distal end of an optical fiber based sensing lead. The amount and/or time of dye release is controlled by a dye-dispensing device which may receive signals, either by telemetric or physical communication lines, from a cardiac pacing device indicating when to initiate dye release. Alternatively, a prescribed amount of dye may be released at predetermined periodic intervals by a fluid dispensing device.

At step 307, the fluorescence emitted by the voltage-sensitive dye is sensed by the optical lead and associated photodetection circuitry, and a determination is made as to whether an action potential is detected from the sensed light signal, step 310. When an action potential is detected from the sensed light signal, a cardiac event sense signal is generated at step 312 for use by control circuitry of the cardiac pacing device in determining an intrinsic heart rate and inhibiting pacing output. Method 300 continues sensing the fluorescence signal at step 307 for the next action potential.

If an action potential is not detected at step 310, a determination is made as to whether a pacing timing interval, referred to as an escape interval, has expired, step 315.

If the escape interval has not expired, NO in step 315, method 300 continues to sense the fluorescence signal at step 307 until either an action potential is detected or the escape interval expires. If the escape interval expires prior to detection of an action potential signal, a pacing pulse is delivered at step 320. Following the pacing pulse, the fluorescence signal is sensed to detect an evoked action potential. If an evoked action potential is detected, as determined at decision step 325, capture is verified and method 300 returns to step 307 to continue sensing local myocardial activity by sensing the fluorescence signal.

If an evoked action potential is not detected following the cardiac pacing pulse, a pacing threshold search is performed at step 330. A pacing threshold search may be performed according to algorithms known in the art. Detection of evoked responses following pacing pulses of varying pulse energies is conventionally performed based on sensing an EGM signal. However, more reliable and accurate evoked response detection may be performed during a pacing threshold search using an optical fiber sensing lead without the associated limitations encountered due to post-pace polarization artifact that occurs when sensing an evoked response on an EGM signal using an electrical lead.

Method 300 of FIG. 16 incorporates the use of optical sensing in place of electrical sensing of cardiac activity to perform known cardiac pacemaker functions such as sensing of intrinsic activity, capture verification, and pacing threshold searches. In an alternative embodiment, action potential sensing using an optical lead is used as an auxiliary form of sensing, enabled only when it is desired to verify information determined from electrically sensed EGM activity or when EGM signal information is indeterminable.

Figure 17:
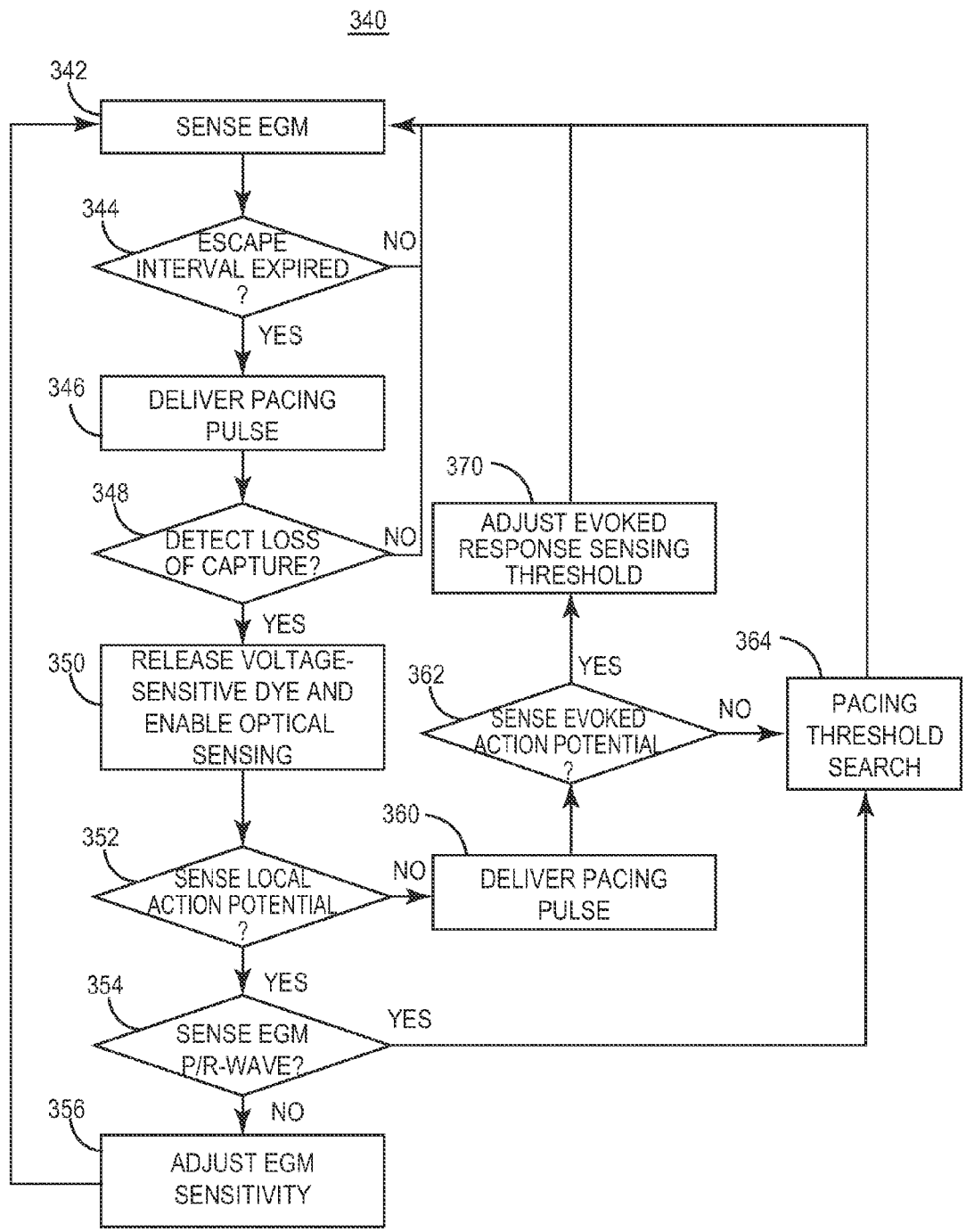
FIG. 17 is flow chart of a method for using optical lead action potential sensing supplementary to electrical EGM sensing during cardiac pacing operations.

FIG. 17 is flow chart of a method for using optical lead action potential sensing supplementary to electrical EGM sensing during cardiac pacing operations. Steps 342 through 348 represent standard cardiac pacing functions based on electrical EGM sensing. At step 342 a cardiac EGM signal is sensed for the detection of atrial P-waves or ventricular R-waves as is customary in the art. If an escape interval expires prior to P-wave or R-wave detection, a pacing pulse is delivered at step 346, and capture verification by EGM evoked response sensing is performed at step 348. If capture is verified by EGM sensing, method 340 returns to 342 to operate according to standard EGM-based sensing and pacing methods.

If a loss of capture is detected at step 348 based on EGM sensing, optical sensing of local action potentials is enabled at step 350. A voltage sensitive dye is released and excitation and detection circuitry is energized to emit the excitation light and receive the emitted fluorescence signal. At step 352, the fluorescence signal is sensed to determine if an intrinsic action potential is present. If a local action potential is detected, method 340 determines if a corresponding, temporally-related cardiac event, either a P-wave or R-wave, was sensed on the EGM signal. If not, undersensing of cardiac events on the EGM signal is likely. The sensitivity of the electrical EGM sensing circuitry is therefore adjusted at step 356. Method 340 then returns to step 342 to continue EGM sensing at the new sensitivity setting. The previously detected loss of capture may have been the result of pacing during physiological refractory following an undersensed intrinsic cardiac event. Thus, optical action potential sensing is used in this case to verify that the absence of an EGM cardiac event and subsequent pacing loss of capture is not due to EGM undersensing of intrinsic cardiac activity.

If a cardiac event is sensed on the EGM signal corresponding to the optically-sensed action potential at step 354, then the EGM sensitivity does not need adjusting and the detected loss of capture may be due to a change in pacing threshold. A pacing threshold search is performed at step 364 and any necessary adjustment to the pacing pulse energy is made. Method 340 returns to step 342 to continue EGM sensing with any necessary pacing output delivered at the new, higher pacing pulse energy.

If an intrinsic action potential is not detected at step 352 following a detected loss of capture based on EGM sensing, another pacing pulse is delivered at step 360 at the same pulse energy as the previous pacing pulse. Optical action potential sensing is performed at step 362 to determine if an evoked action potential occurs following the pacing pulse. If no action potential is detected, the pacing threshold may have changed, and a pacing threshold search is performed at step 364. The previous EGM-based loss of capture detection is appropriate as verified by optical action potential sensing.

If an action potential is sensed at step 362, then the previously detected loss of capture based on EGM sensing at step 348 following a pacing pulse of equal energy could be the result of too high of an evoked response sensing threshold. The evoked response sensing threshold is adjusted at step 370. Method 340 then returns to step 342 to perform cardiac sensing and capture verification based on EGM sensing with the evoked response detection threshold at the newly adjusted setting. In this case, optical action potential sensing is used to verify a detected loss of capture. If loss of capture is not verified, EGM-based capture detection parameters are adjusted as needed. Thus, auxiliary sensing of cardiac activity by optical detection of local action potentials advantageously allows verification of EGM sensing information and diagnosis of EGM undersensing of intrinsic or evoked cardiac events.

Figure 18:
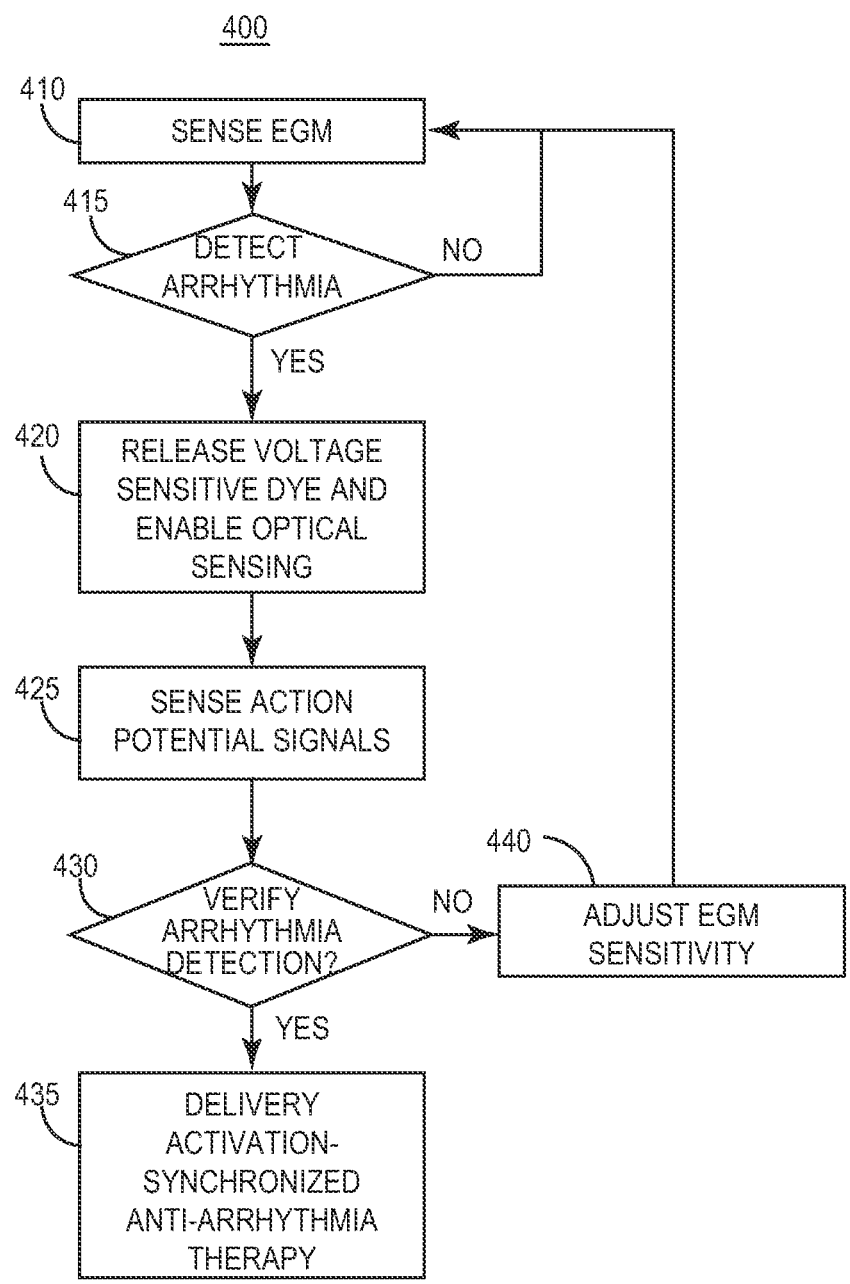
FIG. 18 is a flow chart of a method for using optical fiber lead action potential sensing supplementary to electrical EGM sensing during cardioversion and defibrillation operations of an implantable medical device.

FIG. 18 is a flow chart of a method illustrating the use of sensing action potentials via an optical fiber lead in conjunction with and supplementary to electrical EGM sensing during cardioversion and defibrillation operations of an IMD. Steps 410 and 415 represent customary EGM sensing and arrhythmia detection methods known for use in the art of implantable cardiac rhythm management devices. If an arrhythmia is detected at step 415 based on known arrhythmia detection schemes that rely on EGM sensing, optical action potential sensing is enabled at step 420 by releasing a voltage sensitive dye and energizing excitation and detection circuitry. At step 425, local action potential signals are sensed to determine the local cellular activation and recovery activity. Based on the local activation and recovery times, the provisional EGM-based arrhythmia detection is either verified or cancelled at step 430.

If the arrhythmia detection is verified, local action potential sensing is used to detect activation of local cells such that an anti-arrhythmia therapy may be synchronized with local activation and inhibited during local repolarization as desired to thereby avoid delivering an electrical pulse during the vulnerable period.

If the provisionally detected arrhythmia is not verified by optical action potential sensing at step 430, oversensing of far-field signals or extraneous noise on the sensed EGM signal may have caused an inappropriate arrhythmia detection. EGM sensitivity may optionally be adjusted at step 440 and method 400 returns to step 410 to continue EGM sensing. Thus, optical action potential sensing can be advantageously used to verify EGM-based arrhythmia detection and/or for accurately synchronizing anti-arrhythmia therapies, such as anti-tachycardia pacing therapies, with local myocardial depolarization.

Figure 19:
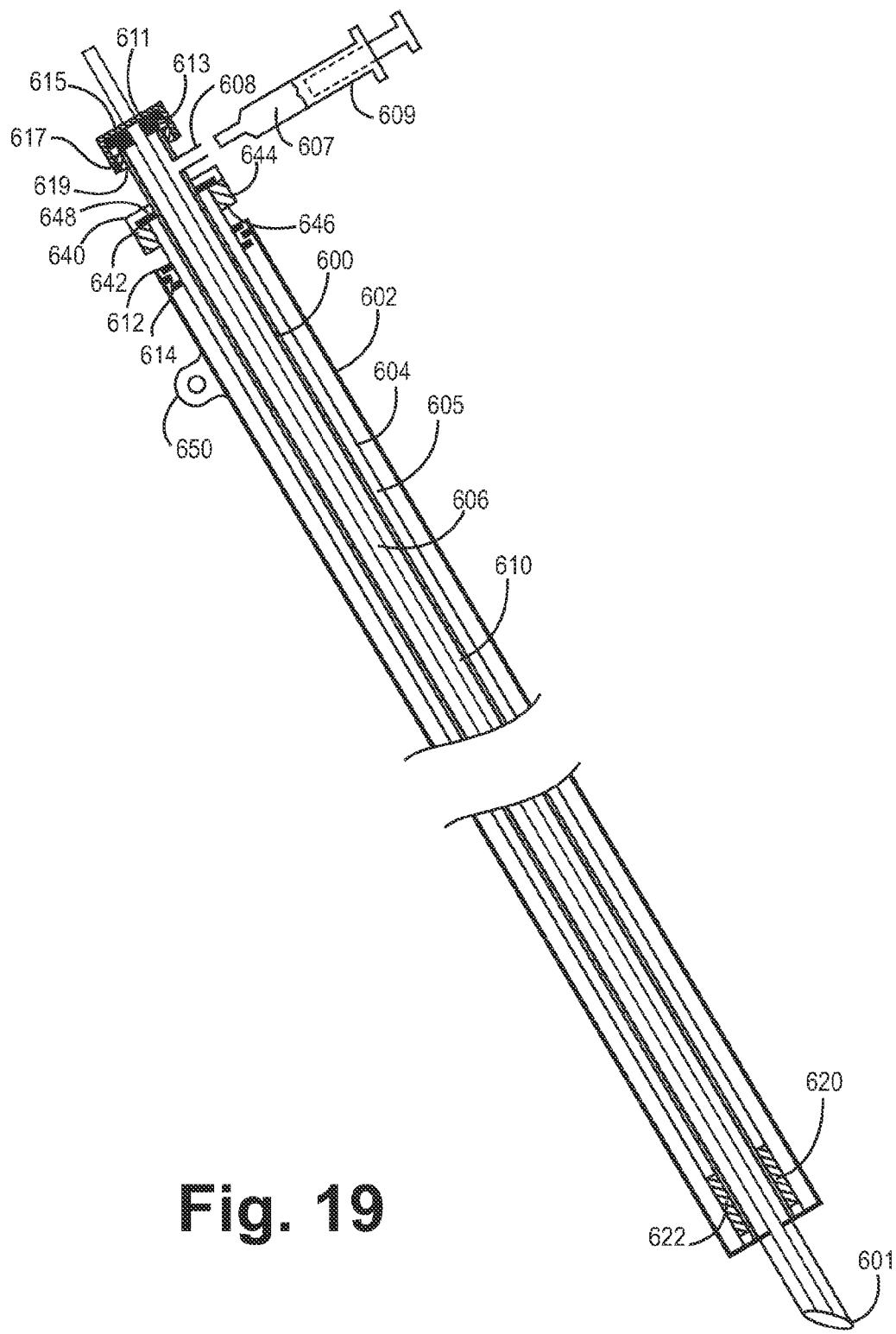
FIG. 19 is a sectional view of an optical fiber-based sensing lead having a mechanism to allow controlled advancement of the optic fiber and a voltage-sensitive dye conduit to a desired tissue depth.

FIG. 19 is a sectional view of an optical fiber-based sensing lead having a mechanism to allow controlled advancement of the optic fiber and a voltage-sensitive dye conduit to a desired tissue depth. The optic fiber 606 is carried in the lumen 610 of a hollow needle 600, which may be a hypodermic-like needle having a sharpened tip 601 for penetrating tissue. The inner diameter of needle 600 is greater than the outer diameter of optic fiber 606 such that needle lumen 610 is larger in diameter than optic fiber 606. The space within lumen 610 formed between optic fiber 606 and needle 600 provides a conduit for the delivery of voltage sensitive dye 607. The dye may be injected into lumen 610 via port 608 using a syringe 609 during acute procedures or a pump as described previously for acute or chronic procedures. The dye is delivered via lumen 610 to a targeted tissue site surrounding needle tip 601.

Needle 600 extends through a lumen 605 formed by a positioning cylinder 604. The cylinder 604 is provided with a threaded surface 620 having screw-like threads extending circumferentially around the inner diameter of cylinder 604 and extending at least a portion of the length of cylinder 604. The threaded surface 620 is dimensioned so as to engage a second threaded surface 622 extending circumferentially around the outer diameter of needle 600 for at least a portion of the length of needle 600. Actuation of the proximal end of cylinder 604, the proximal end being the end opposite the sharpened needle tip 601, in a rotational motion in one direction causes advancement of needle 600, and thereby advancement of optical fiber 606, deeper into a targeted tissue site. Rotation of the proximal end of cylinder 604 in the opposite direction will cause retraction of needle 600 and optical fiber 606 from the targeted tissue site. The position of needle 600 may be maintained at a desired position relative to cylinder 604, i.e., at a desired depth within the targeted tissue, by the cylinder cap 640 and gasket 642 shown in FIG. 19 as will be described in greater detail below. In other embodiments, the position of needle 600 may be stabilized by alternative fixation mechanisms such as a set screw, clamp, or other mechanism for temporarily fixing the longitudinal position of needle 600 with respect to cylinder 604. Alternatively, the position of needle 600 may be maintained at a desired depth within the targeted tissue by friction between the interfacing threaded surfaces 620 and 622.

During rotation of cylinder 604, cylinder cap 640, located on the proximal end of cylinder 604, is in a loosened position. Cylinder cap 640 is provided with a threaded inner surface 644 for engaging with a threaded surface 646 on the proximal, outer circumference of cylinder 604. Needle 600 traverses cylinder cap 640 via an appropriately sized opening 648 in cap 640. Needle 600 freely advances or retracts through opening 648 as cylinder 604 is rotated. Cap 640 is free to rotate with cylinder 604 with respect to needle 600.

Once needle 600 is positioned in a targeted tissue site, cylinder cap 640 is tightened by turning cap 640 with respect to cylinder 604. Tightening of cap 640 causes compression of gasket 642 against the proximal end of cylinder 604. Gasket 642 is contained within cap 640 and positioned around the outer circumference of needle 600. Compression of gasket 642 produces a resultant pressure around the circumference of needle 600 thereby stabilizing the position of needle 600. Thus by tightening cylinder cap 640, the position of needle 600 is stabilized so as to prevent unintentional advancement or retraction of needle 600.

Actuation of cylinder 604 may be performed manually by grasping the proximal end of cylinder 604. It is contemplated that cylinder 604 may be equipped with a handle or grip at or near its proximal end for facilitating rotation of cylinder 604. Threaded surfaces 620 and 622 are shown located near the distal end of the lead, however threaded surfaces 620 and 622 may be positioned interfacing with each other anywhere along the length of the lead. Threaded surfaces 620 and 622 are preferably aligned such that rotation of cylinder 604 allows complete retraction of needle tip 601 within cylinder 604 and rotation of cylinder 604 in an opposite direction allows advancement of needle tip 601 a distance sufficient to reach a desired operating depth within a targeted tissue.

Positioning cylinder 604 extends through the lumen of a tubular lead body 602. Lead body 602 may include an engaging member 614, extending radially inward from the inner diameter of lead body 602, provided for engaging with a second engaging member 612 extending radially outward from the outer diameter surface of cylinder 604. Engagement of members 612 and 614 allow rotational motion of cylinder 604 with respect to lead body 602 but restrict longitudinal motion of cylinder 604 with respect to lead body 602. Thus, torque applied to rotate cylinder 604 will be transferred to needle 600 via engaging threaded surfaces 620 and 622 to thereby cause rotation and resultant advancement or retraction of needle 600. A plurality of paired engaging members 612 and 614 may be provided at locations along the length of cylinder 604 and lead body 602, respectively, to provide additional structural support to the lead and prevent longitudinal motion of cylinder 604 with respect to lead body 602.

Furthermore, interaction of the surfaces of engaging members 612 and 614 may form a fluid-resistant seal so as to prevent or minimize the ingress of body fluids into the lumen of lead body 602. While the presence of bodily fluids within lead body 602 is not expected to adversely affect the functional performance of the optical fiber-based lead, such presence may pose a risk for infection and is therefore be generally undesirable.

Lead body 602 may be grasped during advancement or retraction of needle 600 to prevent movement of lead body 602 relative to the patient's anatomy. Alternatively, lead body 602 may be anchored using sutures or other known anchoring methods to maintain the position of lead body 602 relative to a targeted tissue site. As such, it is contemplated that lead body 602 may be provided with one or more suture rings 650 or other structures through which lead body anchoring sutures may be placed.

Cylinder 604 and threaded surface 620 and engaging member 612 are preferably formed from a biocompatible material having a relatively lubricious surface, such as a fluoropolymer or flouropolymer coated material, which allows smooth rotation of cylinder 604 within lead body 602. The inner surface of lead body 602 and engaging member 614 may also be provided with a fluorpolymer coating to reduce friction between the interfacing surfaces of cylinder 604 and lead body 602. Likewise, threaded surface 622 of needle 600 which interfaces with threaded surface 620 of cylinder 604 may be provided with a fluoropolymer coating so as to allow smooth rotation of cylinder 604 with respect to needle 600. The degree of lubricity between cylinder 604 and lead body 602 and between cylinder 604 and needle 600, i.e., threaded surfaces 620 and 622, may be controlled by the selection of materials and/or coatings used in forming these components.

Needle 600 may be advanced or retracted in a stepwise manner through the targeted tissue to allow measurements at multiple tissue depths. The depth or position of needle 600 relative to cylinder 604 may be known by counting the number of turns applied to the proximal end of cylinder 604 or by providing calibrated markings along the outer surface of needle 600. Optical fiber 606 preferably does not move with respect to needle 600 during advancement or retraction of needle 600. As such, a temporary fixation mechanism may be provided to hold optical fiber 606 in a fixed location with respect to needle 600 during rotation of positioning cylinder 604. In FIG. 19, needle 600 is provided with a cap 611, which when tightened, squeezes down on a gasket 613 captured between the proximal end of needle 600 and needle cap 611. Optical fiber 606 extends through the center opening of gasket 613 and an appropriately sized opening 615 of needle cap 611.

Needle cap 611 is provided with a threaded surface 617 for interfacing with a threaded surface 619 on the outer diameter of needle 600. When needle cap 611 is rotated in one direction, cap 611 is tightened, and, when rotated in the opposite direction, cap 611 is loosened, releasing the grip between gasket 613 and optical fiber 606 allowing adjustment of the position of optical fiber 606 with respect to needle 600. During lead deployment, slight adjustments of the optical fiber 606 position may be needed to obtain a desired signal. Once the signal is acceptable, cap 611 may be tightened to fix the position of optical fiber 606. If the signal deteriorates during chronic use, the position of optical fiber 606 may be readjusted through a minimally invasive procedure by exposing the proximal lead end and loosening needle cap 611 and/or cylinder cap 640 to allow advancement or retraction of optical fiber 606 and/or needle 600, respectively.

Needle cap 611 and gasket 613 will further provide a fluid-tight seal over the proximal end of needle 600, thereby preventing bodily fluids from entering needle lumen 610 through which voltage sensitive dye 607 is delivered. Likewise, cylinder cap 640 and gasket 642 will provide a fluid-tight seal over the proximal end of positioning cylinder 604. The interaction of threaded surfaces 620 and 622 may provide a fluid-resistant seal at the distal end of positioning cylinder 604 to prevent the ingress of bodily fluids from the distal, open end of cylinder 604. Positive pressure, just greater than or equal to the fluid pressure surrounding tip 601, developed within dye-delivery lumen 610 through pumping or injecting dye 607 will resist the ingress of bodily fluids into the distal end of needle lumen 610.

Figure 20:
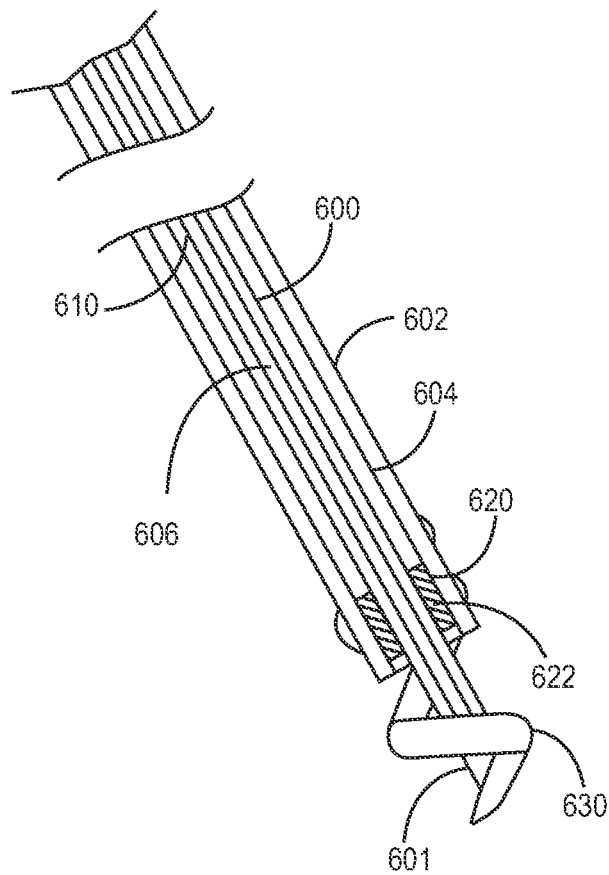
FIG. 20 is a plan view of the distal end of the lead of FIG. 19 further including a fixation member 520 extending from lead body 502.

FIG. 20 is a plan view of the distal end of the lead of FIG. 19 further including a fixation member 630 extending from lead body 602. Fixation member 630 is shown as a sharpened helical member in FIG. 20 but may alternatively be embodied as a hook, tine or other fixation member known for use in anchoring medical leads at a targeted tissue site. Fixation member 630 acts to stabilize the lead position during advancement and retraction of needle 600.

Figure 21:
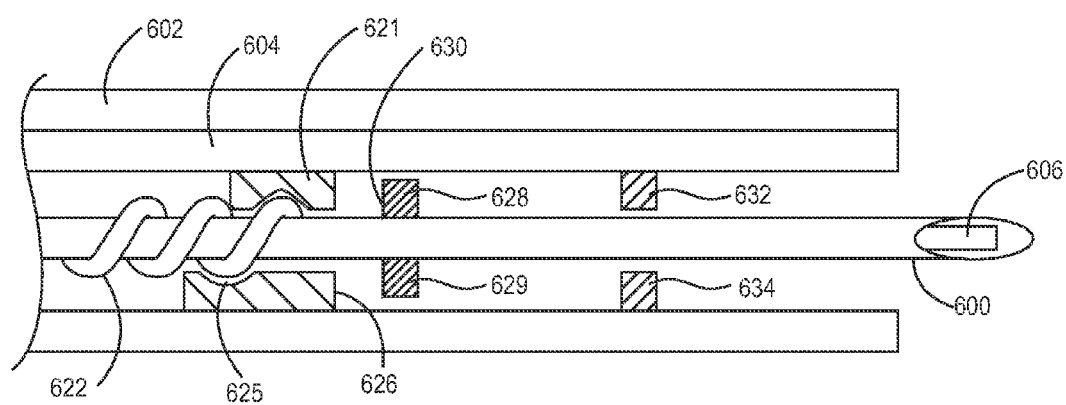
FIG. 21 is a sectional view of the distal end an alternative embodiment of an optical fiber based lead having a controlled advancement mechanism.

FIG. 21 is a sectional view of the distal end of an optical fiber based lead having a controlled advancement mechanism. In this embodiment, needle 600 is provided with a screw-like thread 622 extending circumferentially around the outer diameter of needle 600 for at least a portion of the length of needle 600. Cylinder 604 is provided with a thread guide 621 for engaging thread 622 to actuate needle 600 when cylinder 604 is rotated at its proximal end.

Needle 600 is provided with a stop 628 extending radially outward from the outer diameter of needle 600. Stop 628 includes a proximal face 630 and a distal face 629. Engagement of proximal face 630 of stop 628 with the distal face 626 of thread guide 621 prevents over-retraction of needle 600 into lead body 602. Cylinder 604 is provided with an advancement stop 632 extending radially-inward from the inner diameter of cylinder 604. Advancement stop 632 has a proximal face 634 provided for engaging with the distal face 629 of needle stop 628. Such engagement prevents over-advancement of needle 600 out the distal end of positioning cylinder 604.

Figure 22:
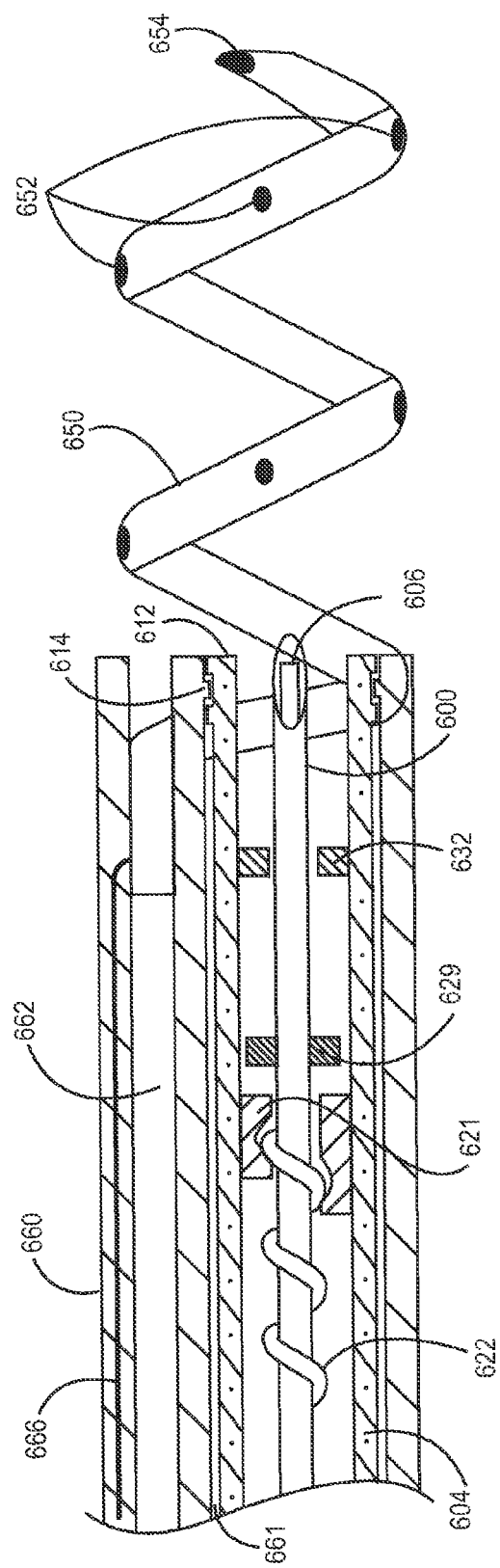
FIG. 22 is an enlarged, sectional view of the distal end of an optical fiber based lead including a hollow lead fixation member for delivering a voltage-sensitive dye to a targeted tissue site.

FIG. 22 is an enlarged, sectional view of the distal end of an optical fiber based lead including a hollow lead fixation member for delivering a voltage-sensitive dye to a targeted tissue site. The lead in FIG. 22 includes a positioning cylinder 604 and needle 600 having a thread guide 621 and thread 622, respectively, as described above in conjunction with FIG. 21. In this embodiment, a pair of engagement members 612 and 614 is shown near the distal end of the lead. Lead body 660 includes engagement member 614 for engaging with member 612 of cylinder 604. As described above in conjunction with FIG. 19, engagement of members 612 and 614 allow rotational motion of cylinder 604 with respect to lead body 660 but restrict longitudinal motion of cylinder 604 with respect to lead body 602 and may form a fluid-resistant seal against the ingress of body fluids.

Lead body 660 is formed as a bilumen tube wherein one lumen 661 is provided for carrying positioning cylinder 604 and needle 600 therein with optical fiber 606 extending there through. The second lumen 662 is an open lumen in communication at its distal end with a hollow fixation member 650, shown in FIG. 22 as a helical fixation member. Fixation member 650 allows the lead to be anchored in the tissue at a targeted tissue site. Fixation member 650 may be provided with an opening 654 at its distal tip and/or one or more apertures 652 at locations along the length of member 650. Lumen 662 is in communication with a pump or syringe at its proximal end to allow administration of a voltage-sensitive dye through lumen 662, into hollow fixation member 650 and out distal opening 654 and/or aperture(s) 652 into surrounding tissue.

Fixation member 650 may optionally function additionally as a stimulating electrode. In such embodiments, fixation member 650 is formed from an electrically conductive material, such as titanium or stainless steel, and is coupled to a conductor 666 extending through, and insulated by, lead body 660. Conductor 666 is electrically coupled to a proximal lead connector which permits electrical connection to a stimulating device.

Figure 23:
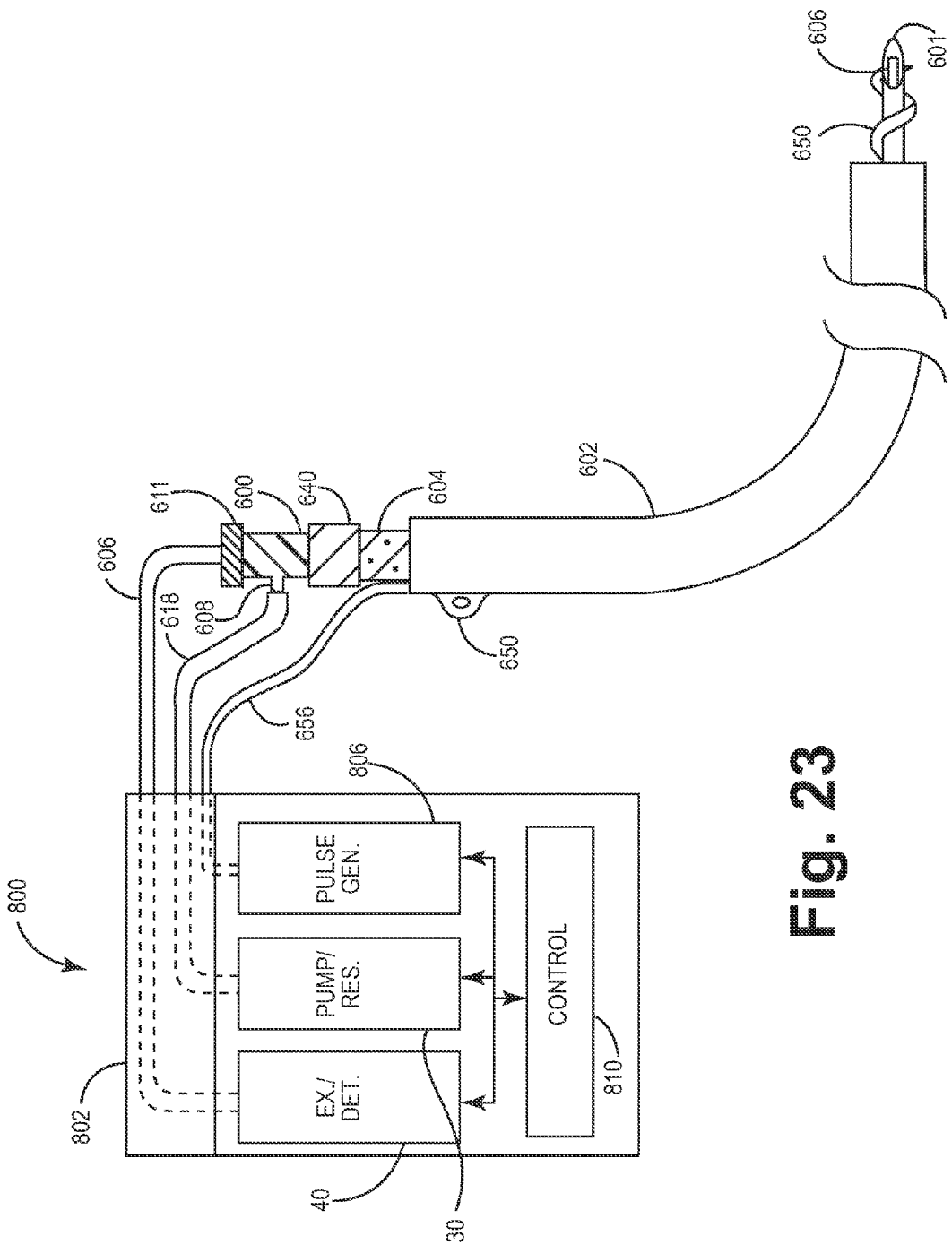
FIG. 23 is a sectional view of an alternative embodiment of an optical fiber-based sensing lead having a mechanism to allow controlled advancement of the optic fiber and a voltage-sensitive dye conduit to a desired tissue depth.

FIG. 23 is a plan view of an optical fiber-based lead coupled to an implantable device. The lead shown in FIG. 20 includes a lead body 602 for carrying a positioning cylinder 604 for advancing and retracting a needle 600 extending there through in the manner as described previously in conjunction with FIG. 19. The lead further includes a fixation member 650 that is coupled to a conductor extending through lead body 602. The lead is coupled to an implantable medical device 800 having a connector block 802 adapted to receive optical fiber 606 extending from needle cap 611; a dye conduit 618 coupled to port 608 projecting from needle 600; and an insulated conductor 656 extending from lead body 650 and electrically coupled to the conductor extending through lead body 650 to fixation member 650.

Optical fiber 606 is thereby optoelectrically coupled to excitation/detection circuitry 40, described previously, included in device 800. Dye conduit 618 coupled via connector block 802 to pump/reservoir 30. Insulated conductor 656 is electrically coupled to pulse generating circuitry 806. In alternative embodiments, the dye conduit 618 may be coupled to a separate device including pump/reservoir 30. Device 800 will typically include control circuitry 810, which may be in the form of a microprocessor, for controlling the operation of excitation/detection circuitry 40, pump/reservoir 30, and pulse generator 806.

Figure 24:
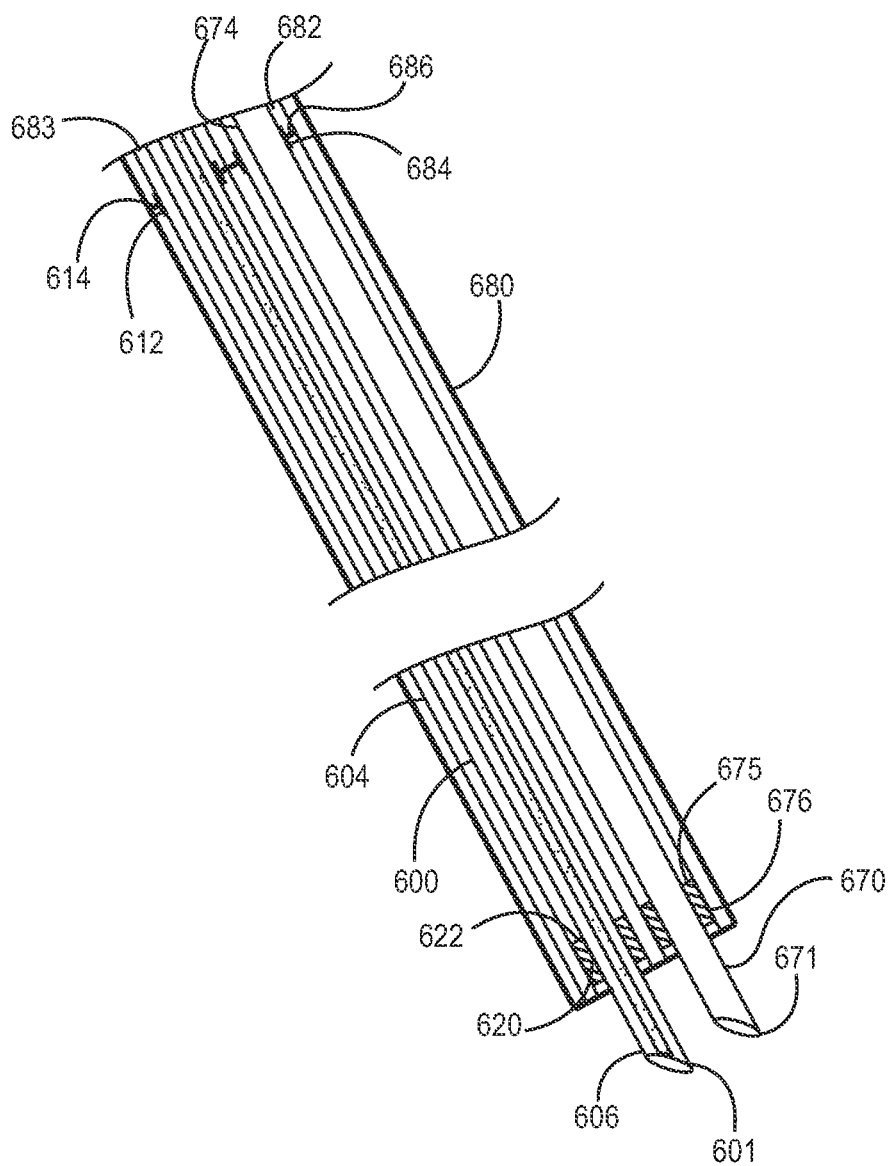
FIG. 24 is a sectional view of an alternative embodiment of an optical fiber-based sensing lead.

FIG. 24 is a sectional view of an alternative embodiment of an optical fiber-based sensing lead having a mechanism to allow controlled advancement of the optic fiber and a voltage-sensitive dye conduit to a desired tissue depth. In FIG. 24, lead body 680 is provided as a bilumen tube having one lumen 683 for carrying positioning cylinder 604 used for advancing or retracting hollow needle 600 through which optical fiber 606 extends as described above in conjunction with FIG. 19.

In this embodiment, however, a second lead body lumen 684 is provided for carrying a second positioning cylinder 670 through which a second hollow needle 670 extends for use in delivering the voltage sensitive dye to a volume of tissue at the targeted tissue site. Needle 670 may be provided with a sharpened tip 671 for penetrating the targeted tissue as it is advanced to a desired depth by rotating cylinder 670 at its proximal end to thereby actuate needle 670 via the interaction of threaded surfaces 676 and 678 in the same manner as described previously for advancing needle 600 in conjunction with FIG. 19.

Engagement members 686 and 684 may be provided on lead body 680 and positioning cylinder 670, respectively, for allowing rotational movement of cylinder 670 with respect to lead body 680 and preventing longitudinal motion of cylinder 670 with respect to lead body 680. Though not shown in FIG. 24, it is contemplated that the lead of FIG. 24 may further include a distal fixation member, such as fixation member 630 shown in FIG. 20, for anchoring lead body 680 relative to a targeted tissue site, and such fixation member may optionally function as a stimulating electrode as described previously.

An optical fiber based sensing lead has thus been described for sensing of action potential signals of excitable tissue. Optical sensing of action potential signals provides numerous advantages over electrical sensing of tissue depolarization signals in that the optical signals are free of noise and artifacts generally associated with electrical sensing such as post-pulse polarization artifacts, far-field electrical signals, electromagnetic noise, electrical signals from other nearby excitable tissue, etc. While the optical fiber based sensing leads and methods for use presented herein have been described according to specific embodiments, it is recognized that numerous variations may be made in the implementation and use of a medical lead that includes an optical fiber for sensing the electrical activity of excitable tissue.

Another embodiment of the claimed invention pertains to monitoring of gene expression. In order to monitor gene expression, tissue (e.g. human tissue, animal tissue etc.) could be co-transfected with a marker gene along with therapeutic gene. In this embodiment, the marker gene is encoded separately or as fusion protein with a therapeutic gene. Co-transfect involves insertion of at least two genes in tissue. At least one of the two genes can express fluorescent protein that can be monitored using an Opti-device like system, as described herein. Monitoring of gene expression applies to all tissue types. Exemplary tissue types include cardiac tissue, muscular tissue etc.

Another embodiment of the claimed invention involves infarct mapping for cell/gene delivery. Infarct mapping is defined as measurement of the size of the infarction. For example, a medical electrical lead can be moved around the heart tissue to detect whether or not the heart tissue exhibits electrical activity. Data is sensed through the medical electrical lead that defines areas where infarction exists compared to tissue where no infarction has occurred.

In yet another embodiment, cells delivered for therapeutic applications are monitored. Specifically, in this embodiment, cells could be transfected with fluorescent marker (e.g. green fluorescent protein (eGFP) or labeled with a dye (e.g. di-8-ANEPPS) or other suitable dyes. A system may then be used for monitoring the fate of cells delivered to the tissue.

Another embodiment of the invention relates to the multifiber system for simultaneously exciting the tissue and collecting of the emitted light. A multifiber system increases the field of view of the system by simultaneously collecting signals from a larger area of the tissue. For example, a multifiber system could simultaneously map the electrical activity of both the infarcted and adjacent tissue.

Figure 25A:
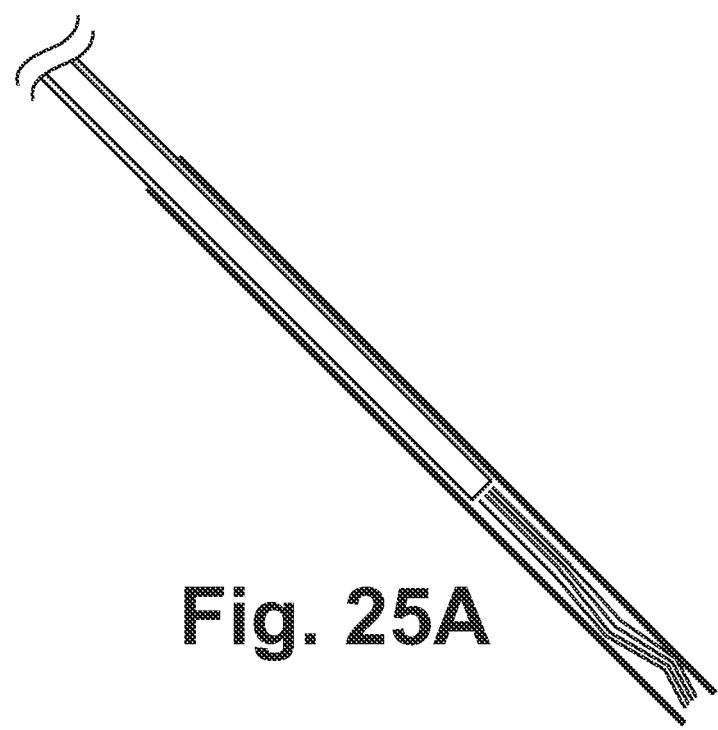
FIG. 25A is a top view of a retracted system of fibers.
Figure 25B:
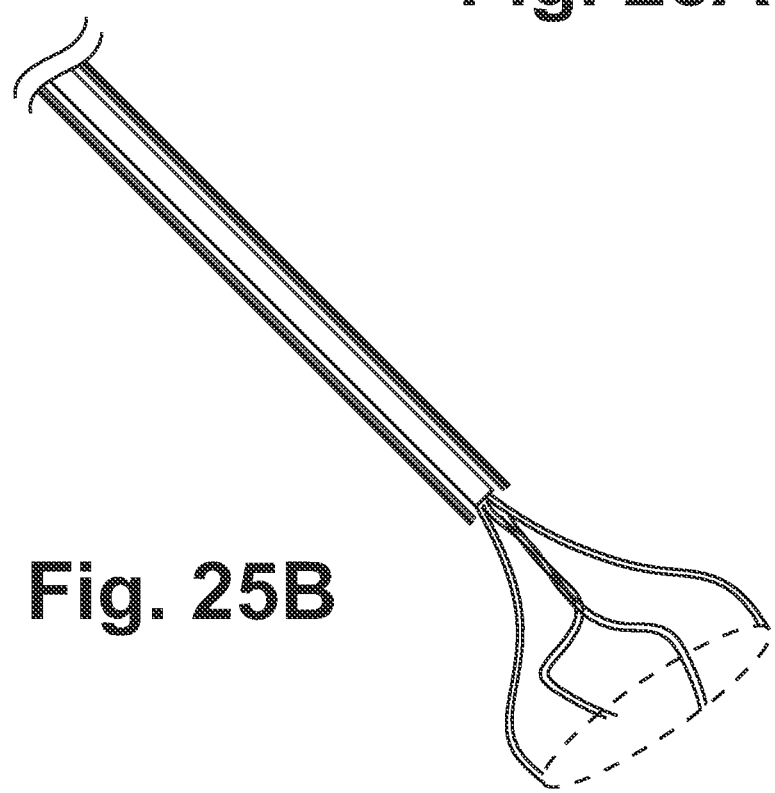
FIG. 25B is a top view of a deployed system of fibers.

Another embodiment of the invention relates to a fiber umbrella that is used to monitor electrical activity and/or gene expression associated with tissue (e.g. cardiac tissue etc.). A fiber umbrella is shown in FIGS. 25A-25B. This process significantly enhances field of view for the physician. For example, the field of view can be increased from 1 millimeter$^2$ (mm$^2$) for a single channel system to 20 mm$^2$ of the umbrella system. Furthermore, the field of view system can be adjusted (e.g. increased or decreased) depending upon the task being performed by the physician.

Another embodiment relates to a detection circuit that contains a single detector and a single emitter along with a switching mechanism (e.g. a mirror for a collector of signals). The switching mechanism is configured to transmit excitation light and collect emitted light (e.g. fluorescent light etc.) from a single fiber of the fiber bundle at a time. The signals from all the fibers are then collected in a sequential manner.

Another embodiment of the claimed invention relates to monitoring voltage activity after transfecting cells with a protein that encodes for a voltage sensitive protein.

Another embodiment of the claimed invention relates to tissue perfusion/ischemia sensing directly in the heart muscle by monitoring tissue $O_2$ saturation.

Another embodiment of the claimed invention relates to a system with multiple wavelength emitters. One such system (e.g. dual wavelength) could be used for sensing tissue perfusion. For example, this system can monitor signals directly in the heart due to the fibers located or inserted in the tissue.

The specific embodiments described herein, therefore, are intended to be exemplary of the concepts of the present invention and not limiting with regard to the following claims.

The invention claimed is:

1. An implantable medical device for monitoring gene expression in a target tissue site co-transfected with a therapeutic gene and a marker gene that expresses a fluorescent protein, the implantable medical device comprising:
   an elongated lead body extending from a proximal end to a distal end adapted to be positioned at the target tissue site;
   a first optical fiber and a second optical fiber, each having a proximal lead end and a distal lead end extending through the elongated lead body;
   wherein the distal lead end of the first optical fiber and/or the second optical fiber comprises a fiber umbrella;
   the first optical fiber transmitting an excitation light to the distal lead end of the first optical fiber positioned at the target tissue site;

the excitation light providing the excitation energy needed for the fluorescent protein expressed by the marker gene to emit a fluorescence signal; and the second optical fiber transmitting the emitted fluorescence signal from the distal lead end of the first optical fiber positioned at the target tissue site to the proximal end of the second optical fiber;

thereby monitoring gene expression in the target tissue site co-transfected with the therapeutic gene and the marker gene.

2. The method implantable medical device of claim 1, wherein the fiber umbrella is retractable within the elongated lead body.

3. The method implantable medical device of claim 1, wherein the first optical fiber for the transmission of the excitation light and the second optical fiber for the transmission of the emitted fluorescence signal comprise a single optical fiber.

4. The method implantable medical device of claim 1, wherein the first optical fiber for the transmission of the excitation light and the second optical fiber for the transmission of the emitted fluorescence signal comprise separate optical fibers.

5. The implantable medical device of claim 1, wherein the first optical fiber for the transmission of the excitation light and the second optical fiber for the transmission of the emitted fluorescence signal comprise a multifiber system.

6. The implantable medical device of claim 5, further comprising single detector and a single emitter along with a switching mechanism, wherein the switching mechanism is configured to transmit excitation light and to collect emitted light from a single fiber of the multifiber system bundle at a time, and wherein the signals from all the fibers of the multifiber system are collected in a sequential manner.

7. The implantable medical device of claim 1, wherein the target tissue site comprises an excitable tissue.

8. The implantable medical device of claim 7, wherein the excitable tissue comprises muscle tissue.

9. The implantable medical device of claim 1, wherein the target tissue site comprises a cardiac tissue.

10. The implantable medical device of claim 1, further comprising excitation circuitry and/or detection circuitry.

11. The implantable medical device of claim 1, connectable to external excitation and/or detection circuitry.

12. The implantable medical device of claim 10, wherein the detection circuitry comprises an emission filter and/or photodetector.

13. The implantable medical device of claim 10, wherein the excitation circuitry comprises a light emitting diode (LED) positioned relative to the proximal end of the first optical fiber.

14. The implantable medical device of claim 1, further comprising a means for converting the emitted fluorescence signal to analog signals.

15. The implantable device of claim 1, further comprising a means for monitoring electrical activity associated with the target tissue site.

16. The implantable medical device of claim 1, further comprising a mechanism to allow controlled advancement of the optical fiber to a desired tissue depth.

17. The implantable medical device of claim 1, further comprising telemetry circuitry.

\* \* \* \* \*